US012718937B2

(12) United States Patent
Moore

(10) Patent No.: US 12,718,937 B2
(45) Date of Patent: Aug. 25, 2026

(54) EVALUATION OF WEARABLE ARTICLES FOR A MEDICAL DEVICE

(71) Applicant: West Affum Holdings Designated Activity Company, Dublin (IE)

(72) Inventor: Mark P. Moore, Kirkland, WA (US)

(73) Assignee: West Affum Holdings DAC, Dublin (IE)

( * ) Notice: Subject to any disclaimer, the term of this patent is extended or adjusted under 35 U.S.C. 154(b) by 20 days.

(21) Appl. No.: 18/793,433

(22) Filed: Aug. 2, 2024

(65) Prior Publication Data

US 2025/0095838 A1 Mar. 20, 2025

Related U.S. Application Data

(60) Provisional application No. 63/538,424, filed on Sep. 14, 2023.

(51) Int. Cl.

| | |
|---|---|
| ***G16H 40/40*** | (2018.01) |
| ***G16H 40/67*** | (2018.01) |
| ***G16H 50/20*** | (2018.01) |

(52) U.S. Cl.
CPC ............. *G16H 40/40* (2018.01); *G16H 40/67* (2018.01); *G16H 50/20* (2018.01)

(58) Field of Classification Search
CPC ......... G16H 40/40; G16H 40/67; G16H 50/20
See application file for complete search history.

(56) References Cited

U.S. PATENT DOCUMENTS

| | | |
|---|---|---|
| 3,724,355 A | 4/1973 | Busch et al. |
| 3,724,455 A | 4/1973 | Unger |
| 4,583,524 A | 4/1986 | Hutchins |
| 4,619,265 A | 10/1986 | Morgan et al. |

(Continued)

FOREIGN PATENT DOCUMENTS

| | | |
|---|---|---|
| DE | 102005060985 A2 | 6/2007 |
| EP | 2305110 A1 | 4/2011 |

(Continued)

OTHER PUBLICATIONS

Ha, The placement position optimization of a biosensor array for wearable healthcare systems, 2019, Journal of Mechanical Science and Technology 33.7 3237-3244 (Year: 2019).*

(Continued)

*Primary Examiner* — Kambiz Abdi
*Assistant Examiner* — Tran N Nguyen
(74) *Attorney, Agent, or Firm* — Propel IP Law, PLLC; Lisa Benado

(57) ABSTRACT

A medical wearable evaluation system is provided that facilitates identifying various design configurations of wearable articles that contribute to the quality of medical data captured for a patient. Medical data analysis may determine particular sets of medical data that more and/or less accurately indicate the medical condition of the patient. Data anomalies present in the medical data are detected and correlated with a design configuration of a wearable article being used by the patient, by retrieving configuration data stored at the wearable article. The evaluation of design configurations may assist in selection of a wearable article and/or adjustment to the wearable article for a particular patient.

19 Claims, 6 Drawing Sheets

(56) References Cited

U.S. PATENT DOCUMENTS 4,666,432 A 5/1987 McNeish et al.
4,698,848 A 10/1987 Buckley
4,928,690 A 5/1990 Heilman et al.
4,955,381 A 9/1990 Way et al.
5,078,134 A 1/1992 Heilman et al.
5,228,449 A 7/1993 Christ et al.
5,348,008 A 9/1994 Bornn et al.
5,353,793 A 10/1994 Bornn
RE34,800 E 11/1994 Hutchins
5,394,892 A 3/1995 Kenny et al.
5,405,362 A 4/1995 Kramer et al.
5,429,593 A 7/1995 Matory
5,474,574 A 12/1995 Payne et al.
5,618,208 A 4/1997 Crouse et al.
5,662,690 A 9/1997 Cole et al.
5,708,978 A 1/1998 Johnsrud
5,741,306 A 4/1998 Glegyak et al.
5,782,878 A 7/1998 Morgan et al.
5,792,204 A 8/1998 Snell
5,902,249 A 5/1999 Lyster
5,913,685 A 6/1999 Hutchins
5,944,669 A 8/1999 Kaib
6,047,203 A 4/2000 Sackner et al.
6,065,154 A 5/2000 Hulings et al.
6,108,197 A 8/2000 Janik
6,148,233 A 11/2000 Owen et al.
6,201,992 B1 3/2001 Freeman
6,263,238 B1 7/2001 Brewer et al.
6,280,461 B1 8/2001 Glegyak et al.
6,287,328 B1 9/2001 Snyder et al.
6,304,780 B1 10/2001 Owen et al.
6,319,011 B1 11/2001 Motti et al.
6,334,070 B1 12/2001 Nova et al.
6,356,785 B1 3/2002 Snyder et al.
6,427,083 B1 7/2002 Owen et al.
6,437,083 B1 8/2002 Brack et al.
6,450,942 B1 9/2002 Lapanashvili et al.
6,529,875 B1 3/2003 Nakajima et al.
6,546,285 B1 4/2003 Owen et al.
6,671,545 B2 12/2003 Fincke
6,681,003 B2 1/2004 Linder et al.
6,762,917 B1 7/2004 Verbiest et al.
7,065,401 B2 6/2006 Worden
7,099,715 B2 8/2006 Korzinov
7,212,850 B2 5/2007 Prystowsky
7,559,902 B2 7/2009 Ting et al.
7,587,237 B2 9/2009 Korzinov
7,753,759 B2 7/2010 Pintor et al.
7,865,238 B2 1/2011 Brink
7,870,761 B2 1/2011 Valentine et al.
7,907,996 B2 3/2011 Prystowsky
7,941,207 B2 5/2011 Korzinov
7,974,689 B2 7/2011 Volpe et al.
8,135,462 B2 3/2012 Owen et al.
8,140,154 B2 3/2012 Donnelly et al.
8,369,944 B2 2/2013 Macho et al.
8,527,028 B2 9/2013 Kurzweil et al.
8,548,557 B2 10/2013 Garstka et al.
8,560,044 B2 10/2013 Kurzweil et al.
8,615,295 B2 12/2013 Savage et al.
8,644,925 B2 2/2014 Volpe et al.
8,676,313 B2 3/2014 Volpe et al.
8,706,255 B2 4/2014 Phillips et al.
8,742,349 B2 6/2014 Urbon et al.
8,897,860 B2 11/2014 Volpe et al.
8,904,214 B2 12/2014 Volpe et al.
8,965,500 B2 2/2015 Macho et al.
9,008,801 B2 4/2015 Kaib et al.
9,084,583 B2 7/2015 Mazar et al.
9,089,685 B2 7/2015 Sullivan et al.
9,119,547 B2 9/2015 Cazares et al.
9,131,901 B2 9/2015 Volpe et al.
9,132,267 B2 9/2015 Kaib
9,265,432 B2 2/2016 Warren et al.
9,345,898 B2 5/2016 Piha et al.
9,408,548 B2 8/2016 Volpe et al.
9,445,719 B2 9/2016 Libbus et al.
9,454,219 B2 9/2016 Volpe et al.
9,579,020 B2 2/2017 Libbus et al.
9,592,403 B2 3/2017 Sullivan
9,598,799 B2 3/2017 Shoshani et al.
9,675,804 B2 6/2017 Whiting et al.
9,724,008 B2 8/2017 Sullivan et al.
9,878,171 B2 1/2018 Kaib
9,895,105 B2 2/2018 Romem
9,901,741 B2 2/2018 Chapman et al.
RE46,926 E 7/2018 Bly et al.
10,076,656 B2 9/2018 Dar et al.
10,192,387 B2 1/2019 Brinig et al.
10,307,133 B2 6/2019 Kaib
10,463,867 B2 11/2019 Kaib et al.
10,589,110 B2 3/2020 Oskin et al.
10,599,814 B2 3/2020 Landrum et al.
2002/0181680 A1 12/2002 Linder et al.
2003/0158593 A1 8/2003 Heilman et al.
2005/0107833 A1 5/2005 Freeman et al.
2005/0107834 A1 5/2005 Freeman et al.
2006/0173499 A1 8/2006 Hampton et al.
2008/0312709 A1 12/2008 Volpe et al.
2009/0005827 A1 1/2009 Weintraub et al.
2010/0007413 A1 1/2010 Herleikson et al.
2010/0298899 A1 11/2010 Donnelly et al.
2011/0022105 A9 1/2011 Owen et al.
2011/0288604 A1 11/2011 Kaib et al.
2011/0288605 A1 11/2011 Kaib et al.
2012/0112903 A1 5/2012 Kaib et al.
2012/0144551 A1 6/2012 Guldalian
2012/0150008 A1 6/2012 Kaib et al.
2012/0158075 A1 6/2012 Kaib et al.
2012/0191476 A1 7/2012 Reid et al.
2012/0265265 A1 10/2012 Razavi et al.
2012/0283794 A1 11/2012 Kaib et al.
2012/0293323 A1 11/2012 Kaib et al.
2012/0302860 A1 11/2012 Volpe et al.
2012/0310315 A1 12/2012 Savage et al.
2013/0085538 A1 4/2013 Volpe et al.
2013/0144355 A1 6/2013 Macho et al.
2013/0231711 A1 9/2013 Kaib
2013/0245388 A1 9/2013 Rafferty et al.
2013/0274565 A1 10/2013 Langer et al.
2013/0317852 A1 11/2013 Worrell et al.
2013/0325078 A1 12/2013 Whiting et al.
2014/0012144 A1 1/2014 Crone
2014/0025131 A1 1/2014 Sullivan et al.
2014/0046391 A1 2/2014 Cowan et al.
2014/0070957 A1 3/2014 Longinotti-Buitoni et al.
2014/0163663 A1 6/2014 Poddar et al.
2014/0324112 A1 10/2014 Macho et al.
2014/0378812 A1 12/2014 Saroka et al.
2015/0039053 A1 2/2015 Kaib et al.
2015/0161554 A1 6/2015 Sweeney et al.
2015/0297135 A1 10/2015 Shoshani et al.
2015/0328472 A1 11/2015 Sullivan et al.
2016/0004831 A1 1/2016 Carlson et al.
2016/0076175 A1 3/2016 Rock et al.
2016/0076176 A1 3/2016 Rock et al.
2016/0082277 A1 3/2016 Foshee, Jr. et al.
2016/0113581 A1 4/2016 Amir et al.
2016/0256104 A1 9/2016 Romem et al.
2016/0283900 A1 9/2016 Johnson et al.
2017/0014073 A1 1/2017 Shoshani et al.
2017/0027469 A1 2/2017 Amir et al.
2017/0036066 A1 2/2017 Chahine
2017/0040758 A1 2/2017 Amir et al.
2017/0162840 A1 6/2017 Pendry
2017/0181703 A1 6/2017 Kaib et al.
2017/0319862 A1 11/2017 Foshee, Jr. et al.
2017/0367591 A1 12/2017 Jorgensen
2018/0116537 A1 5/2018 Sullivan et al.
2018/0117299 A1 5/2018 Gustavson et al.
2018/0184933 A1 7/2018 Sullivan et al.
2018/0185662 A1 7/2018 Foshee, Jr. et al.
2018/0242920 A1* 8/2018 Hresko ................ A61B 5/0006
2018/0243578 A1 8/2018 Volosin

(56) References Cited

U.S. PATENT DOCUMENTS

| | | | | |
|---|---|---|---|---|
| 2018/0361165 | A1 | 12/2018 | Jaax et al. | |
| 2019/0030351 | A1* | 1/2019 | Sullivan | A61N 1/0484 |
| 2019/0030352 | A1 | 1/2019 | Sullivan et al. | |
| 2019/0076666 | A1 | 3/2019 | Medema | |
| 2019/0116896 | A1 | 4/2019 | Armour et al. | |
| 2019/0272726 | A1* | 9/2019 | Kaib | A61N 1/08 |
| 2019/0321650 | A1 | 10/2019 | Raymond et al. | |
| 2019/0385744 | A1* | 12/2019 | Freeman | G16H 40/20 |

FOREIGN PATENT DOCUMENTS

| | | | |
|---|---|---|---|
| JP | 2005507747 | A | 3/2005 |
| JP | 2014500099 | A | 1/2014 |
| JP | 2014526282 | A2 | 10/2014 |
| WO | 9839061 | A1 | 9/1998 |
| WO | 2011/146448 | A1 | 11/2011 |
| WO | 2012/064604 | A1 | 5/2012 |
| WO | 2012/151160 | A1 | 11/2012 |
| WO | 2015/056262 | A1 | 4/2015 |
| WO | 2023107404 | A2 | 6/2023 |

OTHER PUBLICATIONS

Heartstart MRx and XL AED Algorithm—Application Note, Jul. 2001, Edition 2 Philips Healthcare, USA.

Klein, H. U., Goldenberg I., & Moss, A. J., Risk Stratification for Implantable Cardioverter Defibrillator Therapy: the Role of the Wearable Cardioverter-Defibrillator, Clinical update, European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

* cited by examiner

EVALUATION OF WEARABLE ARTICLES FOR A MEDICAL DEVICE

CROSS REFERENCES TO RELATED APPLICATIONS

This application claims the benefit of the filing date of U.S. Provisional Patent Application No. 63/538,424, filed Sep. 14, 2023, the disclosure of which is hereby incorporated herein by reference for all purposes.

This application is related to U.S. patent application Ser. No. 17/900,772, entitled, "Garment Change and Wash Detection In A Wearable Cardioverter Defibrillator (WCD), filed on Aug. 31, 2022, which is hereby incorporated by reference as if set forth in full in this application for all purposes.

FIELD OF THE INVENTION

The present disclosure generally relates to tracking of wearable articles worn by patients as part of a medical device.

BACKGROUND

Wearable medical devices can gather health related patient data while patients wear the medical devices and go about day-to-day activities. Certain medical devices detect and provide critical health information that may require immediate attention, such as lifesaving alerts of cardiac conditions. For example, medical devices used in monitoring for cardiac events may have electrocardiogram (ECG) electrodes that detect electrical impulses of the heart. Some wearable articles used in medical devices can also provide treatment to the patient on the fly based on captured medical data.

Various designs of wearable medical devices may perform differently due to fit, style, types and arrangement of sensors on the wearable and other design configurations. Success of the wearable medical devices can depend on compliance of the patients in using the wearable articles as prescribed by a healthcare provider. Wearable medical devices can be intended for extended and continuous use or for intermittent use. Patient comfort in wearing the medical devices may play an important factor in compliance of the patients and ultimately health outcomes. The wearable articles should fit in a manner that avoids excessive discomfort for the patients.

Sensors on medical devices need to be situated in appropriate positions on or near the patient so that accurate data may be acquired. Often, treatment needs to be provided at specific points in the body. Extended wear medical devices need to allow sensors to remain in place during data capture as the wearable accommodates patient movement.

It would be beneficial to identify wearable article configurations that result in optimal results for the patient. Prompt identification of poor or favorable designs could facilitate changes that improve the outcome of the medical device for the patient.

SUMMARY

A medical wearable evaluation system (also referred to as "wearable evaluation system," "evaluation system," or just "system") is provided to facilitate assessment of various design configurations of wearable medical articles (also referred to as "wearable articles," "wearables", or "support structure") of a medical device worn by a patient. The evaluation system facilitates identification of design configurations of wearable articles that contribute to optimal and/or suboptimal performance in capturing of medical data of the patient.

In some cases, wearable articles for the medical device may be interchangeably worn by a patient. Inaccurate portions of medical data and/or accurate portions of medical data may be determined and matched with a wearable article that produce the problematic or accurate medical data portions. Evaluation of the wearable article can be performed while the patient uses the medical device and changes may be made on the fly. The evaluation of design configuration function may assist in choice of a wearable article that provides optimal performance for the patient.

In some aspects, methods are provided for evaluating design configurations of wearable articles of a cardioverter defibrillator support system. A first wearable article may be provided that embodies a first design configuration and a second wearable article may also be provided that has a second design configuration, different from the first design configuration. In such implementations, a first set of electrocardiogram (ECG) data may be received from first signals captured by first electrodes of the first wearable article being worn by a patient during a first use time period. First configuration data is also received from the first wearable article. The first configuration data indicates that the first wearable article is associated with the first set of ECG data. Further received is a second set of ECG data from second signals captured by second electrodes of the second wearable article being worn by the patient during a second use time period. Second configuration data is also received from the second wearable article indicating the second wearable article is associated with second set of ECG data. Analysis is performed on the first set of ECG data and the second set of ECG data to determine that the first design configuration contributes to data anomalies to a greater extent or lesser extent than the second design configuration contributes to data anomalies.

In some implementations of the method, the first configuration data includes an indication of the first use time period and the second configuration data includes an indication of the second use time period. The first configuration data and second configuration data may be further selected from a group of: at least one wearable article identifier, at least one design feature, and combinations thereof. For example, the first configuration data and/or second configuration data may include at least one design feature selected from the group of: a wearable size, a wearable size adjustment, a wearable style, a biological sensor arrangement, biological sensor contact placement, biological sensor type, and combinations thereof.

The first design configuration and the second design configuration can include different respective sizes of a same style of wearable article. Analyzing the first set of ECG data and the second set of ECG data may include normalizing to adjust for different contact positions of the first electrodes and the second electrodes due to the different respective sizes. In still some implementations, the first design configuration and the second design configuration may include different respective types of wearable articles. In such cases, analyzing the first set of ECG data and the second set of ECG data may include normalizing to adjust for different contact positions of the first electrodes and the second electrodes due to the different respective types.

At times where the first design configuration is determined to contribute to data anomalies to a greater extent a notification may be transmitted to enable the patient to use an additional wearable article having the second design configuration.

The medical wearable evaluation system facilitates evaluating design configurations of at least two wearable articles of the medical device worn by the patient. At least one of the wearable article has a first design configuration and accommodates first biological sensors. At least a second wearable article has a second design configuration and accommodates second biological sensors. The evaluation system further includes at least one computing device having an interface for receiving medical data and configuration data. Logic of the computing device encoded in one or more non-transitory media for execution by one or more processors of the at least one computing device. When the logic is executed, the logic is operable to perform evaluation steps. The steps include receiving a first set of the medical data from signals captured by first biological sensors of the first wearable article being worn by the patient during a first use time period. First configuration data is also received from the first wearable article. The first configuration data indicates the first wearable article is associated with the first set of medical data. The steps further include receiving a second set of the medical data from signals captured by second biological sensors of the second wearable article being worn by the patient during a second use time period. Second configuration data are received from the second wearable article. The second configuration data indicates that the second wearable article is associated with second set of medical data. The sets of medical data are analyzed to determine that one of the design configurations, such as the first design configuration, contributes to data anomalies to a greater extent or lesser extent than the other design configuration, such as the second design configuration.

In some aspects of the system, a sensor that is used in a first wearable article to capture a particular type of medical data may be absent in a second wearable article. In this case, an algorithm used for the analyzing of the medical data from the second wearable article, ignores calculations for the absent sensor.

The steps performed by the logic may further comprise analyzing the first set of medical data and the second set of medical data to determine whether the first design configuration or the second design configuration meets a superior quality threshold. The interface may be configured to a transmit a notification that the first design configuration or the second design configuration is preferred in response to determining that the superior quality threshold is met.

In some implementations of the evaluation system, each of the wearable articles includes an on-board memory to store the configuration data specific for that wearable article.

The evaluation system may further incorporate various aspects of the methods described above for evaluating design configurations of wearable articles of a cardioverter defibrillator support system. Such methods may be used by the evaluation system for other medical events, sensors, and medical devices.

Methods for evaluating a particular design configuration of a wearable article of a medical device may be also used for addressing various medical events. The wearable article for such medical devices have biological sensors that produce signals during a use time period of the wearable article, and from which a set of medical data is received. Based on an analysis of the set medical data, the medical data is determined to indicate a possible medical event experienced by the patient. In response to determining the possible medical event, configuration data is received from the wearable article, indicating the wearable article is associated with the set of medical data. The set of medical data may be analyzed to determine whether the design configuration contributes to data anomalies to meet a poor quality threshold to reject the design configuration or to meet below a superior quality threshold to prefer the design configuration.

Where the design configuration is determined to meet the poor quality threshold, a notification may be transmitted to enable the patient to use an additional wearable article having a different design configuration. Similarly, where the design configuration is determined to meet the superior quality threshold and in response, a notification may be transmitted to enable the patient to use an additional wearable article having a same design configuration. Where the design configuration is determined to meet the poor quality threshold, in some implementations, one or more design features of a plurality of design features of the design configuration may be determined to contribute the poor quality.

BRIEF DESCRIPTION OF THE DRAWINGS

Various implementations in accordance with the present disclosure will be described with reference to the drawings.

FIG. 3*a* shows a first style garment and FIG. 3*b* shows a second style garment, in accordance with some implementations.

DETAILED DESCRIPTION

Figure 1:
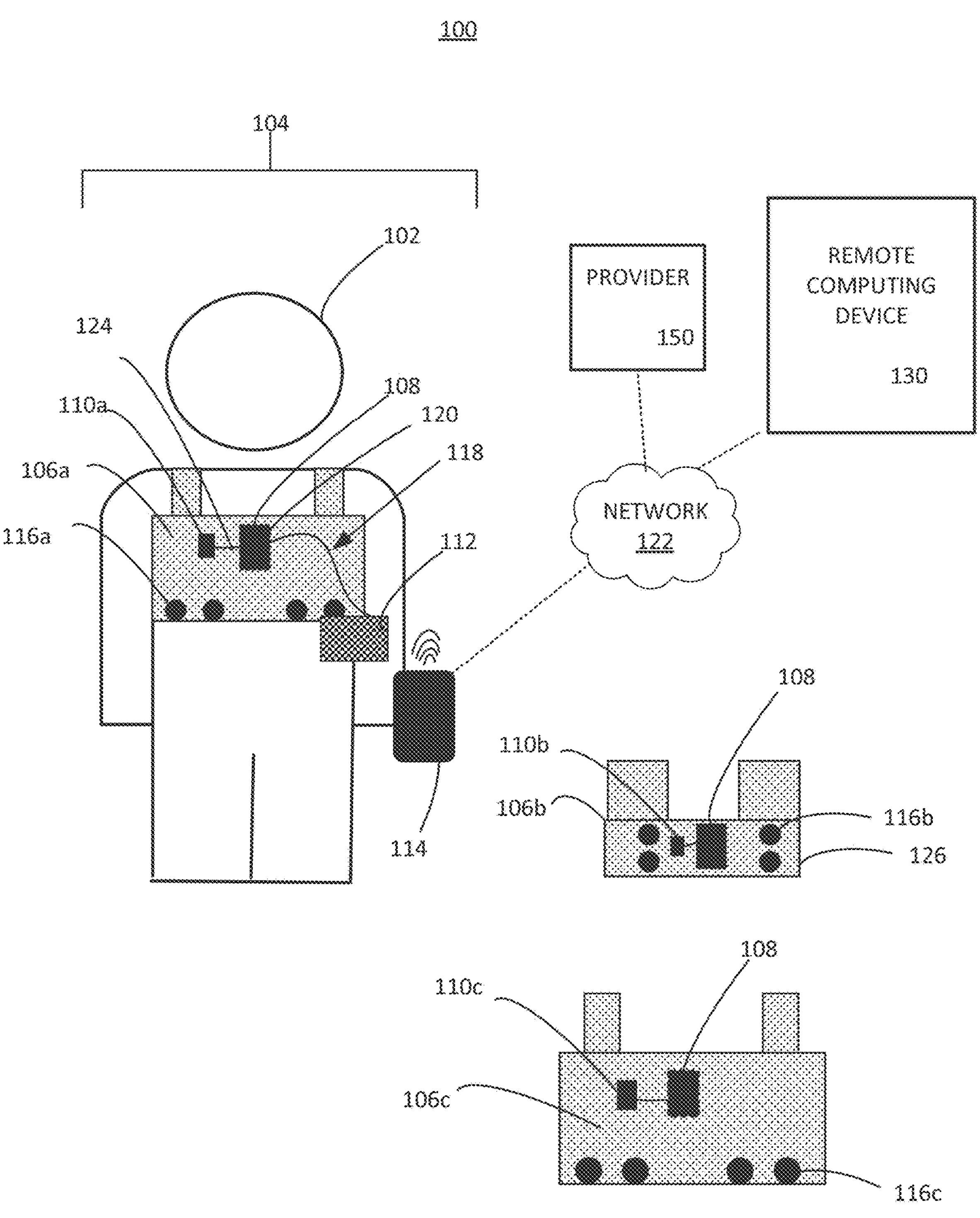
FIG. 1 is a block diagram of an example medical wearable evaluation system for identifying different styles and sensor arrangements of wearable articles worn by a patient, in accordance with some implementations.

In the following description, various implementations will be described. For purposes of explanation, specific configurations and details are set forth in order to provide a thorough understanding of the implementations. However, it will also be apparent to one skilled in the art that the implementations may be practiced without the specific details. Well-known features may be omitted or simplified without obscuring the implementations described. The description of the medical wearable evaluation system provides a framework which can be tailored to individual systems built around the medical wearable evaluation system. Elements may be described in terms of "basic functionality" or varying degrees of functionality.

The medical wearable evaluation system facilitates assessment of a design configuration of a wearable article (also referred to as "wearables") component of a medical device used by a patient to address a medical condition.

Various wearable articles may have different designs features and certain design configurations may be found to perform better than the others in addressing the medical condition. Medical data about the patient are received from signals captured by biological sensors (also referred to as "sensors") associated with the wearable article while worn by the patient during a use time period. The medical data are analyzed by the evaluation system to determine particular sets of medical data that indicate a possible medical event experienced by the patient. Presence of anomaly events in the medical data may also be detected, such as the presence and extent of noise. Anomaly events may include irregularities in the medical data that interfere with the accuracy of the medical data of the patient. The evaluation system associates a particular set of medical data with the wearable article that was worn by the patient at the time of data capture.

The evaluation system collects configuration data from the wearable articles to associate the wearable articles with sets of medical data. Based on the medical data analysis and identification of the wearable article associated with the medical data, the evaluation system determines whether a design configuration contributes to capturing of medical data that includes anomaly events, e.g., noise events. The evaluation system may compare design configurations for a particular patient to determine which wearable article is more or less suitable for the patient based on the anomaly events found for the design configurations.

In some implementations, the evaluation system may determine that a design configuration contributes to data noise to an extent that meets a poor quality threshold, in which case the design configuration may be rejected, or the design configuration contributes to medical data that meet superior quality threshold, in which case the design configuration may be preferred. In some implementations, the evaluation system may determine that a design configuration, for example, having a particular combination of biological sensors type(s) and/or arrangement, leads to more accurate or less accurate episode detection of a medical event in comparison to other design configurations, for example having different types and/or arrangements of biological sensors.

Often, a patient using the medical device is provided with one or more wearable articles. A provider may select wearable articles of various sizes, styles, sensor types, sensor arrangements, etc., according to the needs of the patient. For example, a collection of wearable articles (at least two) having various design configurations may be provided to the patient as part of the wearable medical device. The patient can periodically swap one wearable article for another. Design configurations, for the purposes of this description, include functional design features of a construct of the wearable medical device, observable at the onset of a time period of use of the wearable article by a patient.

At times, a wearable article may allow for adjustments to be made to design features. Intentional adjustments made while a patient uses a wearable article, e.g., manual adjustments by the patient, caretaker, or other user, may trigger a new use time period, and recorded in configuration data. By contrast, random changes that may unintentionally happen during use of a wearable article may not trigger a new use time period for the wearable article. For example, a wearable article design configuration may accommodate a user and/or provider to adjust the fit of the wearable article thereby initiating a new use time period for the adjusted design configuration. The adjustments may be logged as an update to configuration data. The updated configuration data may be retrieved by the evaluation system and associated with medical data captured while the wearable article is in the adjusted design configuration.

In some implementations, medical data captured by the biological sensors of the medical device are regularly reviewed to determine if the patient experiences an episode of a medical event related to a medical condition. Where the medical data meet an episode threshold (e.g. combination of factors in the medical data that indicate a medical event) an episode may be opened at the onset of a medical event and the episode may be closed when the medical data indicates conclusion of the medical event. Quality of the medical data may be critical to correct identification of episodes and/or treatment of the patient. At times, the medical data may include anomalies, such as noise, in which a divergence from expected medical data is determined. Expected medical data may include medical data previously captured for the patient, standard medical data from other patients in similar circumstances as the patient, expected medical data that represents a medical event, medical data predicted by an artificial intelligence model, and other medical data suitable for comparison.

In some situations, an anomaly event in the medical data may occur where a sensor inaccurately detects patient body parameters. For example, when a sensor requires certain contact with the skin of the patient and the sensor does not sufficiently make contact, e.g., leads off event, the data captured by the sensor may include noise events. In some cases, certain types of biological sensors may lead to better identification of an episode than other types of biological sensors for a patient.

Design configurations of wearable articles include design features that impact function of the medical device, in contrast to pure esthetic design differences (e.g., color, fabric pattern) of wearable articles. Different functional design configurations of a wearable article may include various design features such as size, style, type, version, etc., of the wearable article. Design configurations may also include types of sensors, arrangements of sensors in a pattern where each of a type of sensor is placed relative to other sensors, different placements of sensors on the wearable article that result in different contact positions on the patient (e.g., shifting the location of an arrangement of sensors), etc.

Wearable articles may include and/or accommodate different types of biological sensors, e.g., ECG, spO2 from oximeter, temperature from thermometer, where each sensor type captures distinct types of data for a patient. Biological sensors detect health parameters such as patient physiological parameters (heart rate, breathing characteristics, blood oxygenation, body temperature), patient state parameters (body position and orientation), environmental parameters that impact physiology of the patient, and so on. Some types and sizes of sensors may capture a same type of data, such as types of ECG sensors. Some biological sensors may be integrated with the material of the wearable article. Other biological sensors may be removeably attached to the wearable article. In such implementations, the wearable article may accommodate the sensor via an attachment structure, such as a receptacle, strap, fastener, etc. that is adapted for a particular type of sensor. Such removeable sensors specifically held by the wearable article are considered design features of the wearable article in so much as the wearable article is constructed for attachment of the type of sensor.

Design configurations may also include wearables with the same type(s) of sensor(s) but the sensors are arranged in different locations to contact the patient at different points on the body. Some sensor placement configurations are better for some patients and not for other patients. For example, body geometry characteristics can affect how a sensor contacts a part of the body, such as a flat electrode adhering to a patient on folds of skin. Lifestyle or activities of the patient can also affect how a sensor stays firmly against certain parts of the body.

A patient may interchangeably wear wearable articles with different sensor arrangements that provide different contact position on the patient body to lessen skin irritation and increase comfort. Long term use of wearable articles with sensors contacting same points on the body can rub and aggravate the skin over time. Rotating placements of sensors against the skin of a patient by alternating wearable articles with different design configurations can provide comfort and increase the likelihood that a patient will comply with wearing requirement, ultimately improving the performance of the medical device.

At times, two or more wearable articles given to a patient may be different sizes. For example, where a patient is measured to fit in-between regular sizes, it may be uncertain which size of the available wearable articles performs better for the patient. A wearable article having a lower size and another wearable article having next higher size may both be provided to the patient to use.

Fit of the wearable article refers to how the article engages with a part of the patient's body, such as according to a size and/or style of the wearable article. A target fit is assumed to provide a required fit for the medical device to operate effectively. The target fit may include a combination of factors that together meet a predefined fit level, some factors of which may be weighted more than other factors. Fit factors may include particular patient body measurements or a range of body measurements, sensor-to-body contact at a particular location of the body and sufficient contact with the body, patient comfort level, such as, according to a numerical scale, descriptive word ratings, emojis signifying comfort levels, or other mechanisms to assess comfort level, and other fit factors relevant to distinguish a target fit.

The fit of a wearable medical article on a patient can have a direct or an indirect effect on performance of the medical device. Size can be a design configuration that affects the placement of sensors on a patient. For example, where an ill-fitted wearable article results in insufficient sensor to body contact, data acquired by the sensor may be skewed with noise events and health events may be missed. For wearable medical devices that provide treatment to a patient, improper positioning of treatment contact points of the wearable on the body may compromise the treatment of the patient.

Performance of the medical device may also be indirectly affected by an ill-fitting wearable article if a patient fails to comply with use requirements due to discomfort in wearing the wearable article. Comfort may be especially significant for extended wear medical device that is worn continuously, for example, fourteen (14) or more days. A patient may fail to wear the wearable article if, for example, the wearable article is too small, too big, sensors dig into the patient, or there are other problems associated with the fit. To facilitate compliance by the patient with the extended wear regimen, the wearable article should fit comfortably on the patient.

The wearable article may be configured for extended wear for prolonged continuous use of a wearable medical article by a patient. In some implementations, the length of time can be over two weeks. The term "continuous use" or variations thereof, is understood to include daytime use, which may be from several hours of the day and/or at night, to full daytime hours and full nighttime use. In some implementations, the wearable article of the medical wearable evaluation system may be worn without stop except for temporary daytime removal, for example, during brief activities that may expose the wearable article to potentially adverse conditions such as extensive water contact, e.g., bathing or swimming, cleaning of the wearable article, etc. Thus, "continuous use" is intended to include such brief periods of non-use.

Different designs of wearable medical articles may include various combinations of styles and sizes. In some example, a garment type of the wearable article can include various styles for patients with breasts, styles for patients without breasts, vest styles, a half-vest style, t-shirt styles, etc. Other types of wearable articles may be in the form of a harness, adhesively attached housing, etc. Various styles of a particular type of wearable medical articles may have distinct arrangements of components and/or features, cover different body parts, or other variations that may affect function of the wearable article on a body.

The present evaluation process performed by the medical wearable evaluation system includes capturing medical data from biological sensors of the first wearable articles being worn by the patient during various use time periods. Configuration data may be received from the wearable article while being worn by the patient. At times, the configuration data may be received after use of the wearable article (e.g., shortly after removal). For example, during a treatment of a medical event, the wearable article may be removed by a medical support person and the configuration data may be retrieved from the wearable article after removal.

The configuration data assists in identifying the wearable article, as well as design configuration that correlate with particular medical data. The configuration data further enables identifying biological sensor arrangements, sensor types, wearable size, etc. associated with medical data that involve noise in the medical data. The medical data associated with use of each wearable article are analyzed to determine that one design configuration may contribute to data noise more than another wearable article. At times, design configuration differences may include changes in combinations of design features, such as a combination of different size, sensor types, etc. In other implementations, different design configurations among wearable articles used by a patient include a single feature change, such as size or style.

In some conventional wearable medical devices, a review of medical data may be performed after a medical event and such conventional devices do not include functionality to correlate medical data to wearable article. For example, such conventional devices may not be able to determine whether poor data quality is associated with a particular wearable article in use at the time of capture of the medical data. The present evaluation system addresses such correlation between medical data quality and wearable article including design configurations. Other benefits of the evaluation system will be apparent from the further description of the system and methods, as described below.

The wearable article of the present evaluation system may be all inclusive in which the wearable article integrates the functionality required to provide medical monitoring and/or care to the patient. The terms, "medical device" or "wearable medical device" as used herein refer to one or more physical devices including one or more wearable articles, and/or software components. In some implementations, the medical device may be a medical monitoring device to monitor the patient for medical condition(s) and/or a medical treatment device to provide medical treatment to the patient.

The wearable article may include a programmable memory device to store configuration data and to transfer the configuration data via a communications interface. Configuration data include various design features (e.g., the size of the wearable article, the type or style of the wearable article, sensor type, arrangement, position of sensors and other programmable data), wearable article identifiers (e.g., a unique identification or serial number of the wearable article, the manufacturer of the wearable article) and/or time of use of the wearable article. Configuration data may be programmed into the memory device during manufacture and read at runtime by the wearable medical device. The memory may be a ROM, nonvolatile programmable memory.

A communications interface to retrieve the configuration data may be wired, e.g., inter-integrated circuit (I2c), serial peripheral interface (SPI), etc., or may be a wireless interface. A wired interface can enable power to be supplied to various electronic components of the wearable article. The configuration data can be read from the wearable article for each medical event so that the particular wearable article being worn when the event occurred can be identified. This data in turn can be used to determine if the design configuration of the wearable article used was a factor in the event (e.g., events in which there is a lot of noise, which may have resulted from poor wearable article fit).

FIG. 1 shows an example of the medical wearable evaluation system 100 that includes a medical device 104 that incorporates wearable articles 106*a*, 106*b*, and 106*c* available for use by a patient 102. Each of the wearable articles include an on-board memory unit 110*a*, 110*b*, and 110*c*, to store configuration data and which can interface with one or more removeable components of the medical device, such as an electronic module 120 (also referred to as a "hub"), main unit 112, and patient communication device 114. The evaluation system 100 may further include a remote computing device 130 (which may be collectively one or more remote computing devices) located away from the site of the medical device 104 and in communication with the medical device 104 across a network 122. The remote computing device 130 may communicate with the medical device 104 via various connections, such as connecting directly to the medical device 104 or through intermediary devices such as the patient communication device 114. Components of the evaluation system 100, such as remote computing device 130, may also be in communication with a health support provider 150, such as the physician for the patient that provides personalized healthcare attention to the patient.

Some examples of the medical device 104 may include a wearable cardioverter defibrillator (WCD), such as the ASSURE wearable defibrillator system available from Kestra Medical Technologies, Inc., Kirkland, WA. Other WCD devices are possible for use in the medical support system. A WCD may also provide pacing therapy for detected bradycardia and/or asystole. The wearable medical device may further include monitoring devices that check patient parameters with or without integrated treatment components, such as Wearable Cardiac Monitoring system (WCM) by Kestra Medical Technologies, Inc., Kirkland, WA, Holter type of monitors, mobile cardiac outpatient telemetry (MCOT) systems by Philips Company, etc. Other medical devices employing a wearable article may be used with the medical wearable evaluation system to address a variety of medical events and medical conditions.

Various implementations of the medical device 104 may include a variety of components that are removeable from and or insertable in the wearable article, as well as components that are fixed. Wearable article components that are integrated and non-removeable may include certain biological sensors 116*a*, 116*b*, and 116*c*, such as ECG's, (however, some sensors may be removeable coupled to the wearable article) and memory unit 110*a*, 110*b*, and 110*c* and receptacle 108 (described below). Integrated components, for example, may be sewn into fabric of the wearable article.

Removeable components may be connected to at least some of the integrated components of the wearable article, held by attachment structures or material of the wearable article, or otherwise removeably coupled to the wearable article. Removeable components may further be in electronic communication (wired or wireless) with at least some of the integrated components. Wearable article components that are removeable may include electronic module 120 (described below), various detachable sensors (not shown), and connector cable 118. Further, removeable components may be coupled to particular integrated components, such as electronic module 120 connected to memory unit 110*a* via memory cable 124 and held by the wearable article via receptacle 108.

In some design configurations, the wearable article may include various coupling features for coupling removeable components to particular locations on the wearable article, such as cable guides to align cables between the electronic module 120 and the main unit 112 along the spine and shoulders of the patient. In some implementations, the cable guides may be elastic loops with snap fasteners that may be secured over the cable to the wearable article and released to remove the cable. The design configuration of the wearable article may further include one or more pockets, such as receptacle 108, or openings to place electrical components, various sensors, wires, etc. within the wearable article. For example a pocket may be provided at the top of the belt that abuts a back portion of the wearable article. The pocket or opening may include a fastener to close the pocket or opening. There may be other components of the medical device external to the wearable article that can be coupled to, e.g., plug into, various components of the wearable article, such as main unit 112 via cable 118.

The wearable article may include receptacle 108 structured to accept the electronic module 120 that connects to the wearable articles 106*a*, 106*b*, and 106*c* to receive inputs from and send instructions to various medical device components including medical data from sensors 116*a*, 116*b*, 116*c*. The receptacle 108 may contain one or more electrical contacts to electrically connect various electrical components to the wearable articles 106*a*, 106*b*, and 106*c* that may be used by a treatment unit, such as electrodes and a control module that can be used for defibrillation treatment. In some implementations, receptacle 108 may contain a hard plastic lining to receive the electronic module 120. In other implementations, rather than a receptacle 108, another connector may be used to physically and electrically connect the electronic module to the wearable articles 106*a*, 106*b*, and 106*c*.

Further, in accordance with implementations of the present disclosure, the receptacle 108 may include a communications interface. In some implementations, the electronics module 120 when positioned in the receptacle 108 makes wired connectivity (via the aforementioned electrical contacts in the receptacle 108) and is configurable to access the memory unit 110*a* (when use also accesses memory units 110*b*, 110*c*) of communications interface via memory cable 124. Further, in some implementations, the electronic module 120 when received in receptacle 108 may also provide power to the communications interface. Further examples of a vest-style and/or shirt-style wearable article is described in U.S. Pat. No. 10,926,080, entitled, "Wearable Cardioverter Defibrillator with Breast Support."

The patient 102 may swap out the use of various of the wearable articles 106*a*, 106*b*, and 106*c* of the medical device 104 to restart different use time periods defining the period of time a wearable article is used by the patient. For example, the wearable article 106*a* being worn by the patient (currently in-use) may be discontinued to be used and a next wearable article 106*b* or 106*c* may be put into use. The use time periods may be characterized by a starting point when the wearable article is connected, such as coupling to an electronic portion of medical device, such as the main unit 112 and/or electronic module 120, and subsequent ending point when the same wearable article is disconnected, such as from the main electronic portion, such as the main unit 112 and/or electronic module 120. In some implementations, wearable article 106*a*, 106*b*, and 106*c* may put into use, for example, by connecting memory cable 124 between the respective memory units 110*a*, 110*b*, and 110*c* and electronic module 120. In some implementations, a new use time period may be initiated by a substantive adjustment for a currently in-use wearable article, made to a design feature of the design configuration that alters the function of the design feature.

An indication of the use time period for a wearable article that is in-use, e.g., worn and connected to electrical components of the medical device, may be stored as configuration data. For example, the use time period indication may be stored in memory units 110*a*, 110*b*, and 110*c* on-board in each respective wearable article. The indication of the use time period may be in various formats, such as date and time of the starting and ending of use, length of use, etc.

In some implementations, the indication of the use time period may match a timestamp associated with a particular set of medical data captured by sensors of the wearable article. Matched times may be used to identify the wearable article in-use at the time of capturing the medical data. For example, the timestamp may fall within a period of time that the wearable article is used. The timestamp of the medical data may specify a time that signals were captured by biological sensors forming the medical data. In some cases, the timestamp may specify a time that medical data is received by a certain component of the medical device, such as main unit 112. Matching of the timestamp with use time period may include factoring any time lag required for processing and/or transfer of the medical data into the timestamp data. In this manner, the time that medical data are collected may be synced with time of receipt of configuration data that correlates with an in-use wearable article.

Wearable articles 106*a*, 106*b*, and 106*c* illustrated in the example of FIG. 1, each have a different design configuration. Wearable articles 106*a* and 106*c* have a same wearable style that may be described as a shirt-style, and wearable article 106*b* has a different wearable style that may be described as a vest-style. Wearable article 106*c* is a different size that is a larger size than wearable articles 106*a*, 106*b*. Wearable article 106*c* also has different sensor contact placements (spots that the sensors contact on the body of the patient) in a same sensor arrangement on the wearable article as wearable article 106*a*.

Vest-style wearable 106*b* has a belt 126 that contains biological sensors 116*b*, e.g., electrodes in a sensor arrangement that is a double vertical row of pairs of the sensors. Shirt-style wearables 106*a*, 106*c* contain biological sensors 116*a*, 116*c* in a sensor arrangement that is a horizontal single row along a bottom length of the wearable.

Sensors 116*a*, 116*b*, 116*c* may be coupled to the wearable article by various mechanisms, such as attachment to a fabric of the wearable or couple to a structure that is part of the wearable. In some implementations, the sensors 116*a*, 116*b*, 116*c* may be positioned within, fastened to, or on a fabric layer that faces the patient 102. In some implementations, the belt 126 may contain electrical contacts for electrode sensors to connect. The electrode sensors may be used, for example, by the electronic module 120 to determine an ECG of the patient.

Further, in some implementations the sensors may be positioned on the wearable article at different places compared to other wearable articles. As previously mentioned, the sensor arrangement and/or sensor contact positions may be stored as configuration data in the memory unit to be used in some implementations in determining whether the design configuration is related to certain events, e.g. noise events, indicated by medical data of the sensors.

Some styles of wearable articles may be selected to address certain patient characteristics, such as body variation information (e.g., differences from typical bodies caused by injury, birth defects, surgery, etc.), body shape, hot spots (due to garment friction or being too tight), mobility (e.g., wheelchair bound), posture, gait, visible physical or medical idiosyncrasies, or atypical body contours, etc. Other patient characteristics that may be considerations in selecting a wearable style include patient preferences, such as preferred style or size of wearable article, patient lifestyle descriptors, such as athletic, generally sedentary, personality, temperament, psychological conditions, touch sensitivities, etc., compliance information such as an ability of patient to put on or take off wearable article, etc.

The medical device 104 may further include a patient communication device 114 held by the patient in a location that is at or near the patient. The patient communication device, such as a mobile device, e.g., a smart phone, tablet or other personal device, may be controlled by the patient, a residential caretaker of the patient, friend or relative of the patient, or other support persons. The patient communication device 114 may be a general purpose communication device that has other uses in addition to the medical device. In other implementations, the patient communication device 114 may be dedicated to function just for the medical device.

In some implementations, patient communication device 102 may also accept various user inputs, such as without limitation, audio, e.g. voice recognition, touchscreen, switch input with an on-screen or external keyboard, head mouse, gesture recognition, facial recognition, movement tracker, eye movement tracker, smart buttons, trackball, track pen, pen tablet, pen, stylus, and hand mouse. The input may include a user applying touch, voice, click, tap, type, gestures, movement (e.g., moving an eye, arm, body), and other actions.

The patient communication device 114 may receive and/or send signals via a wireless connection with main unit 112 and/or other medical device components. In some implementations, the patient communication device 114 may receive signals, such as encoded medical data, configuration data, identification of a wearable article that correlates with the medical data, etc., from the wearable article 106*a*, main unit 112, and other medical device components. In some implementations, the patient communication device 114 may run a software program to perform at least some of the evaluation process described herein. The patient communication device 114 may assess such data locally and/or transmit such data via network 122 to the remote computing device 130 and/or provider 150 for remote storage and/or assessment.

The remote computing device 130 may include a processor that accesses relevant evaluation process data, e.g., medical data, configuration data, etc. stored in a memory. The processor may perform one or more of the described steps to evaluate design configurations of wearable articles.

In some implementations, steps for evaluating design configurations may be distributed among evaluation system components. Some steps may be performed locally at the patient medical device. For example, medical data analysis and/or identification of the wearable article that correlates with the medical data may be performed by the main unit 112 and/or patient communication device 114. For local actions, analysis, e.g., identification of an optimal design configuration, may be transmitted to the remote computing device and/or provider via network 122 for further action and/or storage. In still some implementations, identification of the wearable article may be performed locally, and determination of noise events and determination of a design configuration that contributes to the data noise to a greater extent may be performed remotely by remote computing device 130. In still some implementations, identification of the wearable article that correlates with sets of medical data may be performed locally. In some implementations, medical data may be transmitted from the remote computing system 130 to provider 150. The provider 150 (such as a medical professional at a medical facility) may perform medical data analysis to identify medical event episodes and/or discern data anomalies, e.g., noise events. The provider 150 may send such anomaly identification to the remote computing device 130 to match the noise event with the particular wearable article and assess which of a plurality of associated design configurations provides more accurate medical data results for the patient.

The network 122 may be used to communicate between local medical device components and remote components. The network 122 may include one or more WANs (Wide-Area Networks) and/or LANs (Local-Area Networks), which may be wired and/or wireless. In some examples, the network 122 may include the Internet and/or one or more cellular networks, among other networks. For example, the network 122 may provide a connection, for example, through a local network to a host computer or to data equipment operated by an Internet Service Provider (ISP). The ISP in turn provides data communication services through the world wide packet data communication network (the "Internet").

The network 122 may operate according to one or more communication protocols, such as Bluetooth™, LTE (Long-Term Evolution), CDMA (Code Division Multiple Access), WiMax (Worldwide Interoperability for Microwave Access), WiFi (Wireless Fidelity), WiFi Direct (Wireless Fidelity Direct), EDGE (Enhanced Data rates for GSM (Global System Mobile) Evolution), 3G (Third Generation), 4G (Fourth Generation), HTTP (Hyper-Text Transfer Protocol), TCP (Transmission Control Protocol), SIP (Session Initiation Protocol), device contact based transfer protocols, device movement based pairing protocols, and other communication protocols. Although the network 122 is shown as a single networks, it should be understood that the network 122 may include multiple, distinct networks that are themselves communicatively linked. The network 122 could take other forms as well.

The depictions in FIG. 1 is not to be construed as limiting components of the medical wearable evaluation system 100 and how the evaluation system 100 is implemented. The evaluation system 100 can be implemented in different ways with additional or less devices/components. For example, in some implementations, all medical wearable evaluation actions may be performed locally and the remote computing device may be employed for storage of evaluation results or the remote computing device 130 may be left out of the evaluation system 100 altogether.

Figure 2:
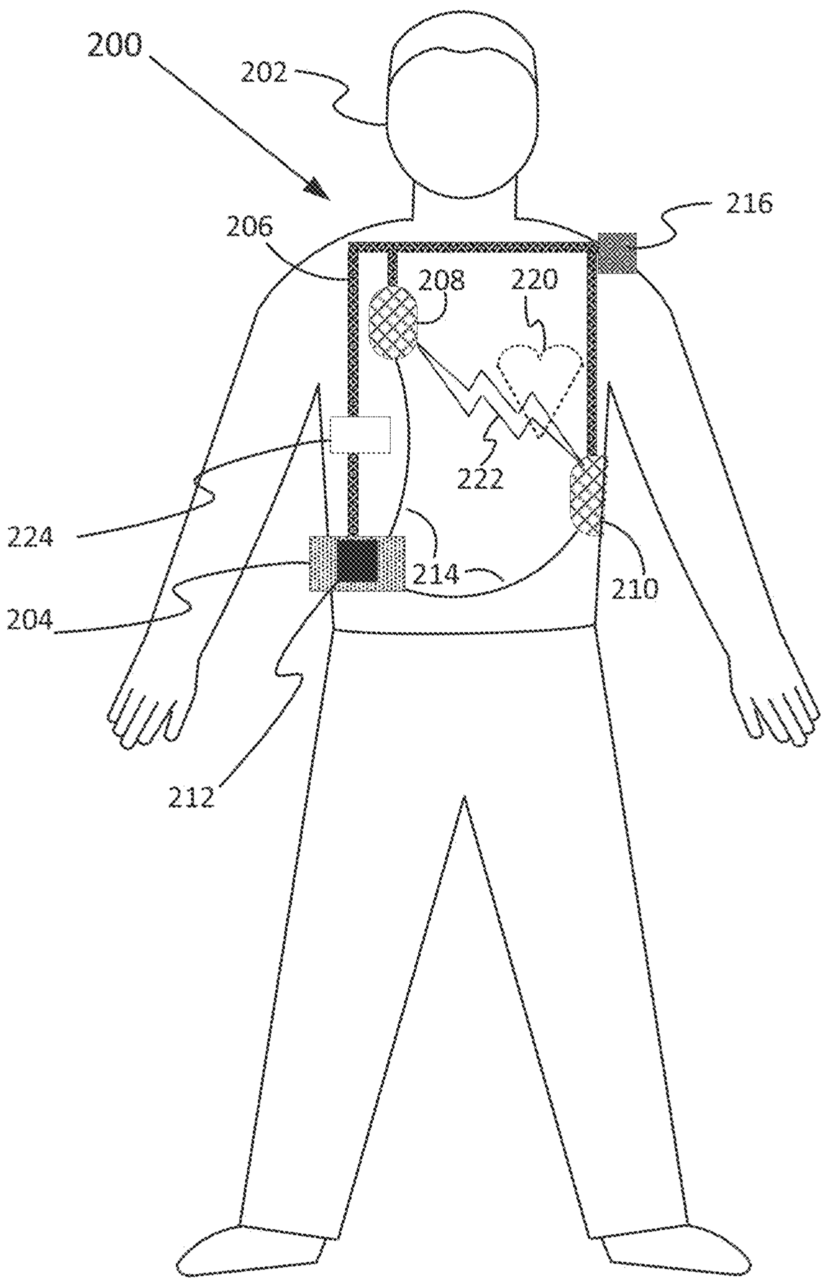
FIG. 2 is a schematic diagram of an example of the wearable medical device for therapy of a patient, in accordance with some implementations.

FIG. 2 shows an example of a medical device 200 including a wearable article 206 that can be employed in the medical wearable evaluation system. The medical device 200 in this example is in the form of a wearable cardioverter defibrillator (WCD) configured to provide cardiovascular treatment to a patient 202 (ambulatory patient). In particular, FIG. 2 depicts components of the evaluation system that implements a WCD and is made according to implementations.

The medical device 200 configured as a WCD may treat the patient 202 who is wearing the designated components of the medical device 200 by electrically restarting the heart 220 if needed. The components of the medical device 200 can be provided separately as modules that can be interconnected, or can be combined with other components, and so on. Defibrillating can be by the medical device 200 delivering an electrical charge to the patient's body in the form of an electric shock. The electric shock can be delivered in one or more pulses.

The patient 202 may also be referred to as a wearer of components of the medical device 200. The patient 202 may be ambulatory, in which the patient 202 can if desired and capable, walk around, be in a vehicle, and so on, while wearing the wearable component(s) of the medical device 200. In other words, the patient 202 is not necessarily bed ridden. The patient 202 may also be considered a "user" of the medical device 200. The term "user" may not be exclusive to the patient 202. For instance, a user of the medical device 200 may also be a clinician such as a doctor, nurse, emergency medical technician (EMT), or other similarly tasked and/or empowered individual or group of individuals. In some cases, a user may even be a bystander. The particular context of these and other related terms within this description should be interpreted accordingly.

The wearable article 206 can be configured to be worn by the ambulatory patient 202 for at least several hours per day, and also during the night, for at least several days, and even a few months. The wearable article 206 may be worn for shorter stretches of time or longer stretches of time, such as a year with intermittent periods of break, such as for washing or while a patient participates in an activity that requires removal of the wearable article such as swimming. At times, multiple different wearable articles are swapped, as described herein. It will be understood that the wearable article 206 is shown only generically in FIG. 2, and in fact partly conceptually. FIG. 2 is provided merely to illustrate concepts about the wearable article 206, and is not to be construed as limiting how the wearable article 206 is implemented, or how it is worn.

The wearable article 206 can be implemented in many different ways. For example, the wearable article 206 can be implemented in a single component or a combination of multiple components. In implementations, the wearable article 206 could include a vest, a half-vest, a garment, etc. In such implementations such items can be worn similarly to analogous articles of clothing. In implementations, the wearable article 206 could include a harness, one or more belts or straps, etc. In such implementations, such items can be worn by the patient around the torso, hips, over the shoulder, etc. In implementations, the wearable article 206 can include a container or housing, which can even be waterproof. In such implementations, the wearable article can be worn by being attached to the patient's body by adhesive material, for example as shown and described in U.S. Pat. No. 8,024,037. The wearable article 206 can even be implemented as described for the wearable article of US Pat. App. No. US2017/0056682, which is incorporated herein by reference. Of course, in such implementations, the person skilled in the art will recognize that additional components of the medical device 200 can be in the housing of a wearable article instead of being attached externally to the wearable article, for example as described in the US2017/0056682 document. There can be other examples.

Implementations of FIG. 2 include a main unit 204, which can be also called an electronics module or hub. In implementations, the main unit 204 implements an external defibrillator. In some situation, the main unit 204 may implement an external pacer instead of, or in addition to, an external defibrillator. In implementations that include a pacer, the medical device 200 may detect when the patient's heart rhythm slows down or when the patient has asystole, and the pacer may pace to increase the heart rate. In such implementations, the medical device 200 may pace the patient first, and hopefully not have to resort to the full intervention of defibrillation. Of course, if the patient does not respond to the pacing, a defibrillation shock may be delivered.

The implementations of FIG. 2 also include therapy electrodes 208, 210, which are electrically coupled to main unit 204 via electrode leads 214. More than two therapy electrodes are possible. The therapy electrodes 208, 210 are also sometimes referred to herein as defibrillation electrodes or just electrodes. Therapy electrodes 208, 210 may also serve as sensing electrodes to sense cardiovascular parameters. Other sensing electrodes that do not provide treatment to the patient, may be present for cardiovascular parameter sensing, such as outside monitoring device 216 described below.

The therapy electrodes 208, 210 can be configured to be worn by the patient 202 in a number of ways. For instance, the main unit 204 and the therapy electrodes 208, 210 can be coupled to the wearable article 206, directly or indirectly. In other words, the wearable article 206 can be configured to be worn by the ambulatory patient 202 so as to maintain at least one of the therapy electrodes 208, 210 on the body of the ambulatory patient 202, while the patient 202 is moving around, etc. The therapy electrodes 208, 210 can be thus maintained on the body by being attached to the skin of the patient 202, simply pressed against the skin directly or through garments, etc. In some implementations the therapy electrodes 208, 210 are not continually pressed against the skin, but become biased against the skin upon sensing a condition that could merit intervention by the medical device 200. In addition, many of the components of the main unit 204 can be considered coupled to the wearable article 206 directly, or indirectly via at least one of the therapy electrodes 208, 210.

When the therapy electrodes 208, 210 make good electrical contact with the body of the patient 202, the main unit 204 can administer, via the therapy electrodes 208, 210, a brief, strong electric pulse (not shown) through the body. The pulse is also known as defibrillation pulse, shock, defibrillation shock, therapy, electrotherapy, therapy shock, discharge, discharging, etc. The pulse is intended to go through and restart the patient's heart 220, in an effort to save the life of the patient 202. The defibrillation pulse can have an energy suitable for its purpose, such as at least 100 Joule ("J"), 200 J, 300 J, and so on. For pacer implementations, the pulse could alternately be depicting a pacing pulse. At least some of the stored electrical charge can be caused to be discharged via at least two of the therapy electrodes 208, 210 through the ambulatory patient 202, so as to deliver to the ambulatory patient 202 a pacing sequence of pacing pulses. The pacing pulses may be periodic, and thus define a pacing period and the pacing rate. There is no requirement, however, that the pacing pulses be exactly periodic. A pacing pulse can have an energy suitable for its purpose, such as at most 10 J, 5 J, usually about 2 J, and so on. The pacer therefore is delivering current to the heart 220 to start a heartbeat. In either case, the pulse has a waveform suitable for this purpose.

Some conventional defibrillators may decide whether to defibrillate or not based on an ECG signal of the patient. However, in some implementations, the main unit 204 may initiate defibrillation, or hold-off defibrillation, based on a variety of inputs from various sensors of the medical device 200, with the ECG signal merely being one of these inputs.

A medical device 200 that implements a WCD according to implementations can collect data about one or more parameters of the patient 202. For collecting such data, the medical device 200 may optionally include at least an outside monitoring device 216. The device 216 is called an "outside" device because it could be provided as a standalone device associated with the wearable article and not within the housing of the main unit 204. The outside monitoring device 216 can be configured to sense or monitor at least one local parameter. A local parameter can be a parameter of the patient 202, or a parameter of the medical device 200, or a parameter of the environment.

For some of these parameters, the outside monitoring device 216 may include one or more sensors or transducers. Each one of such sensors can be configured to sense a parameter of the patient 202, or of the environment, and to render an input responsive to the sensed parameter. In some implementations the input may be quantitative, such as values of a sensed parameter; in other implementations the input may be qualitative, such as informing whether or not a threshold is crossed, and so on. Such inputs about the patient 202 are also called physiological inputs and patient inputs. In implementations, a sensor can be construed more broadly, as encompassing more than one individual sensors.

Optionally, the outside monitoring device 216 may be physically coupled to the wearable article 206. In addition, the outside monitoring device 216 may be communicatively coupled with other components that are coupled to the wearable article 206, such as with the main unit 204. Such communication can be implemented by the outside monitoring device 216 itself having a communication module, as will be deemed applicable by a person skilled in the art in view of this description.

A medical device 200 that implements a WCD according to implementations preferably includes sensing electrodes, which can sense an ECG and/or other cardiovascular related parameters of the patient. In implementations, the outside monitoring device 216 may include such sensing electrodes. In those implementations, the sensed parameter of the patient 202 may include the ECG of the patient, the rendered input can be time values of a waveform of the ECG signal, and so on.

In implementations, one or more of the components of the shown medical device 200 may be customized for the patient 202. This customization may include a number of aspects. For instance, the wearable article 206 can be fitted to the body of the patient 202. For another instance, baseline physiological parameters of the patient 202 can be measured for various scenarios, such as when the patient is lying down (various orientations), sitting, standing, walking, running, and so on. These baseline physiological parameters can be the heart rate of the patient 202, motion detector outputs, one for each scenario, etc. The measured values of such baseline physiological parameters can be used to customize the medical device 200, in order to make diagnoses more accurate, since patient bodies differ from one another. Such parameter values can be stored in a memory of the medical device 200. Moreover, a programming interface can be made according to implementations, which receives such measured values of baseline physiological parameters. Such a programming interface may automatically input the measured values in the medical device 200, along with other data.

The wearable article 206 is configured to be worn by the ambulatory patient 202 so as to maintain the therapy electrodes 208, 210 on a body of the patient 202. The wearable article 206 can be advantageously implemented by clothing or one or more garments. Such clothing or garments need not have the function of covering a person body as a regular clothing or garments do, but the terms "clothing" and "garment" are used in this art for the wearable article 206 and associated components of the medical device 200 intended to be worn on the human body in the similar or same way as clothing and garments. Such clothing and garments of a medical device 200 can be of different sizes for different patients, and even be custom-fitted around the human body. Regular clothing can often be worn over portions or all of the wearable article 206.

In addition, and in accordance with implementations of the present disclosure, the wearable article 206 may include a wearable communications interface 224 that includes a memory device (such as memory device 110*a*, 110*b*, 110*c* in FIG. 1) for storing configuration data of the wearable article. In some implementations, the main unit 204 may also include a main communications interface 212 configured to communicate with the wearable communications interface 224 of the wearable article 206 in order to request or receive the configuration data of the wearable article 206.

The configuration data can include a unique ID or Serial Number of the garment, the manufacturer of the wearable article (such as garment manufacturer), the size of the wearable article, the type or style of the wearable article, etc. and can be programmed during manufacturing into the memory device and read at runtime by the medical device 200. The memory device may be a ROM, or in some implementations the memory device can be a nonvolatile programmable memory (e.g., a 1-Wire® EPROM or EEPROM available from Analog Devices, Wilmington MA) that can be programmed with additional data after the patient begins wearing the wearable article. In some implementations, the main unit 204 may include a processor than can use main communications interface 212 to read/write configuration data from/to the memory device of wearable communications interface 224. The wearable communications interface 224 could be wired (I2c, SPI, etc.) or wireless. In wireless implementations of wearable communication interface 224, the main communications interface 212 of the main unit 204 would also be wireless and be configurable to wirelessly communicate with devices remote of the evaluation system. In wired implementations of wearable communication interface 224, the main unit 204 may be configured to power the wearable communication interface 224.

In some implementations, one or more expanded capabilities can be implemented in the medical device 200 system. For example, the wearable article may have configurable ECG electrode locations, or there may be different ECG locations for different styles of wearable articles. The configuration data can include the ECG electrode location information. By providing the patient with multiple wearable articles that are designed to accommodate different ECG electrode positions, electrodes on the various wearable articles contact the skin in a different area, reducing a risk of patient skin irritation. Some patients experience skin irritation if the ECG electrodes are in contact with a particular patch of skin for a prolonged period of time. Wearable articles with different ECG electrode locations can alleviate this skin irritation issue. Any ECG algorithm adjustments necessary, due to differing electrode placement, may be triggered by the main unit 204 reading the wearable article configuration data.

As described, the evaluation system may support a range of wearable articles with different sensors that are wireless or wired. In some implementations, the medical device may determine how to collect data from these variety of sensors through use of configuration data from each wearable article (communication identifier, personal identification number (PIN), etc.) that specifies design configurations including various sensors associated with select wearable articles. For example, the medical device may determine from configuration data that a particular sensor was present and then use the medical data acquired by that sensor in assessing the patient condition and/or evaluating a design configuration. If a particular sensor is not present on a wearable article, as apparent from the configuration data, the communication interface may be directed to not attempt to communicate with the missing sensor. As such an algorithm used for the analyzing of the medical data may safely ignore portions of the algorithm that is used for calculations, e.g., detecting medical events, anomalies, quality checks, etc., involving signals specific to a sensor type that is absent according to the design configuration, without risking skipping important captured medical data. Ignoring portions of an algorithm directed to absent sensors may assist the processes to run more efficiently, saving resources and calculation time. For example, where a type of medical data that is specific to the missing sensor, and no other sensors of the wearable article detects that type of medical data, the software skips algorithms that are specific to the type of medical data of the missing sensor.

The configuration data that includes identifiers to the wearable article, such as a unique identifier, can enable tracking of performance of individual wearable articles. For example, wearable article identifier data may be retrieved from the wearable article from event logs and/or reports so that performance differences between wearable articles assigned to a patient can be evaluated. In some implementations, usage metrics may also be calculated for each wearable article to record how the wearable article is used by the patient, such as how often the wearable article is worn and washed.

In some cases, the configuration data can be read from the wearable article for each medical event that the patient experiences according to data interpretation. The particular wearable article being worn when the medical event occurred can be captured. In some instances, the configuration data includes identifier to the wearable article and excludes detailed descriptions of the design configuration of the wearable article. The identifier can be cross-referenced with stored data that describes the design configuration of each wearable article. The cross-reference information in turn may be used to determine if the design configuration of a particular wearable article was a factor in the event (e.g., events in which there is a lot of noise, which may have resulted from poor garment fit).

The evaluation system may detect patterns of medical data anomalies that correspond with a particular design configuration and by evaluating the pattern, determine that the design configuration is the likely cause of the data anomalies. In some implementations, the causal relationship between the design configuration and the data anomaly may be further determined by ruling out other extraneous factors that may influence medical data accuracy. For example, if similar data anomalies are detected as other variable change, such as actions of the patient at the time of the time of the data anomaly, then particular patient actions may be ruled out as an causing the data anomaly. Various design configurations of wearable articles may also be compared to determine if certain one or more design configurations (i.e. target design configuration(s)) result in cleaner or more accurate medical data than other design configurations. In turn, the patient may be directed to wear and/or provided with wearable articles having the target design configuration.

According to some implementations, the wearable article can be implemented as disclosed in U.S. Pat. No. 10,926,080, which is incorporated herein by reference for all purposes.

Figure 3A:
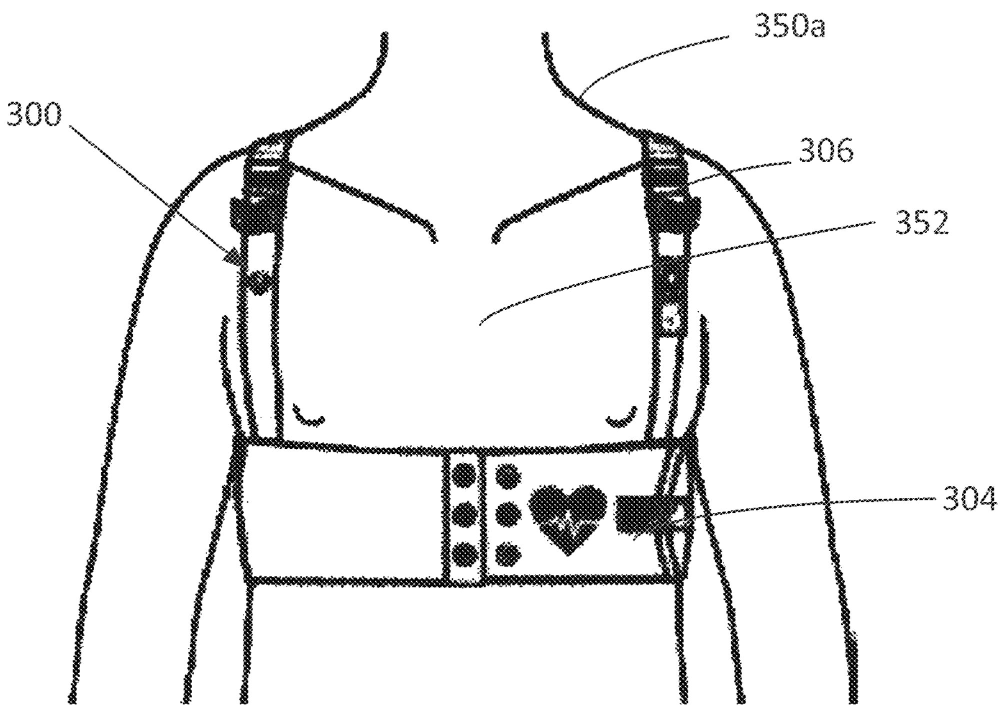
FIGS. 3*a* and 3*b* are schematic diagrams of examples of different styles of wearable articles in the form of garments, where
Figure 3B:
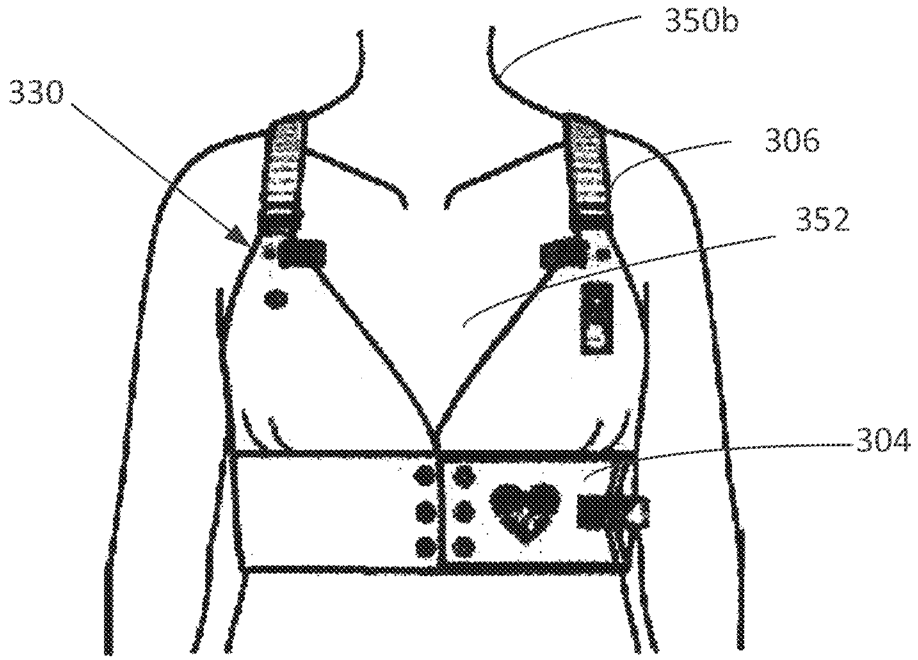

FIGS. 3*a* and 3*b* are schematic diagrams of examples of different styles of a vest garment type of wearable articles worn by different patients 350*a*, 350*b*, where FIG. 3*a* shows a wearable article 300 having a first style garment with an under-bust style and FIG. 3*b* shows another wearable article 330 having a second style garment with a bust cover style.

The vest garment type wearable article may include a fabric material base, which may house a variety of components for the medical device. The wearable article 300, 330 has a main body portion 304 fitted around a torso 352 of the respective patient 350*a*, 350*b* and two shoulder straps 306 with one shoulder strap designed to fit over each shoulder of the respective patient 350*a*, 350*b* from the front side of the patient to the back side of the respective patient.

In various design configurations of the wearable article, adjustments may be made to the wearable article to vary the fit. For example, the shoulder straps 306 may be adjustable to accommodate a range of torso lengths. In some implementations, design configuration data may include the selected wearable size adjustments of the straps while being worn during a use time period. For example, the wearable article may also be implemented with a single shoulder strap, for example, that may wrap around the neck or around one shoulder at an angle, or as a full vest rather than having shoulder straps.

The main body portion 304 (also referred to as a belt) may be installed to fit snug around the torso with the shoulder straps 306 holding the main body portion 304 in place onto the torso 352 of the patient 350*a*, 350*b*. In this manner, the wearable article 300, 330 may encircle the patient 350*a*, 350*b* without a need for adhesives to attach the wearable article or sensors onto the patient. The main body portion 304 may be enclosed around the torso with fasteners, such as snaps, buttons, hook and loop, clasps, clamps, buckles, catchers, ties, etc., or with flexible fabric or elastic to allow stretch for slippage onto the torso. Other enclosures are possible.

In some implementations, the main body portion 304 may be adjustable to loosen or tighten around the torso of the patient. For example, a series of horizontally spaced rows of fasteners may enable a patient, provider or caretaker to select a row that provides level of snugness onto the body. The selected wearable size adjustment of the main body portion e.g., fastener row employed, may be included in configuration data for the wearable article as worn during a particular use time period.

The under-bust style wearable article (Style 1) 300 may use long shoulder straps 306 to engage the wearable article under the bust than the bust cover style wearable article (Style 2) 330. The bust cover style wearable article (Style 2) includes additional fabric to cover the bust area of the patient 350 and short shoulder straps 306 to engage the wearable article above the bust area. The style may be decided based on various patient specific data such as body shape, e.g., more pronounced bust girth, gender (although not necessarily dispositive to selecting a style), patient preference, patient comfort, etc.

The depictions in FIGS. 3A and 3B are not to be construed as limiting the styles of wearable articles or how the wearable articles are implemented or worn. The wearable article 300, 330 of a torso fitted wearable article can be implemented in many different ways to engage with at least a portion of the torso of the patient. For example, it can be implemented in a single element or a combination of multiple elements, which may be coupled together. In some implementations, wearable article 300, 330 could include a harness, one or more belts or straps, etc. that fit on a torso or other accessible parts of the patient. The wearable article 300, 330 can also be worn around hips, over the shoulder, around appendages, etc. In implementations, such items can be worn similarly to analogous articles of clothing. Such items can be worn parallel to or underneath other articles of clothing.

One or more sizes of wearable articles may be assigned to a patient to achieve a target fit. The size of each wearable article provided to a patient may be stored in memory of the wearable article as configuration data for the wearable article. The assigned size may be based on body measurements obtained for the body part(s) to be worn by the wearable article and treatment contact points on the body, in which sensors and/or treatment providing components of the wearable article needs to make contact with the body to be effective. For example, in some implementations a vest-type wearable article for cardiac medical conditions may be employed on a torso of the patient with electrodes spaced proximal to the heart. In such torso-wearing articles, patient body measurement data may include a bust measurement (bust girth), under-bust measurement, waist size, torso length, and/or patient height.

A target fit may be presented in quantitative or qualitative terms to signify conformity of various fit factors of the wearable article, to operations parameters needed for proper performance of the medical device as it is intended to be used. For example, operations parameters may include application of a sufficient amount of a substance, e.g. electrode gel or conductive solution, on a particular body part, proper communication between electrodes, etc. The target fit enables wearable component-to-body contact such that a wearable component, e.g., electrode, to be in a proper position for monitoring or treatment. Other wearable components needing proper placement may include a display screen, user controls, wire leads, etc. . . . Fit factors may include body contact type factors, such as an amount of body surface area in contact by the wearable component, pressure applied to the component against body, the component positioned within target region of the body. Other factors may include how the wearable article falls on the body, such as, gaping of the wearable fabric relative to the body, tightness on body, fabric wrinkling or bunching, restricting of body movement, etc. Still other factors may relate to environmental interference of the sensor e.g., ECG electrode, to properly detect, such as reduction of noise interference by a properly fitted wearable article.

Some example sizes based on under-bust circumference measurements may include: Size 1A, 1B: 28"-32"; Size 2A, 2B: 31.5"-35.5"; Size 3A, 3B: 35-39"; Size 4A, 4B: 38.5-42.5"; Size 5A, 5B: 42"-46"; Size 6A, 6B: 45.5"-49"; Size 7A, 7B: 48.5"-52". Size A indicates a first style wearable article and size B indicates a second style wearable article.

In some cases, the body measurements may fall between two sizes and both lower and higher sized wearable articles may be selected. In still some cases, a body measurement that falls above or below a fit level may not be within any available size of wearable article. To illustrate in the example sizing chart shown, an under-bust measurement that falls less than 28 inches or greater than 52 inches may indicate that a class of wearable article may not be available for the patient. In such circumstances, size accommodations may be made, such as the closest size(s) may be selected, a custom sized wearable article may be made, or a closest size wearable may be size adjusted, e.g., tightened or loosened. These size accommodations may be included in the configuration data for the wearable article.

Figure 4:
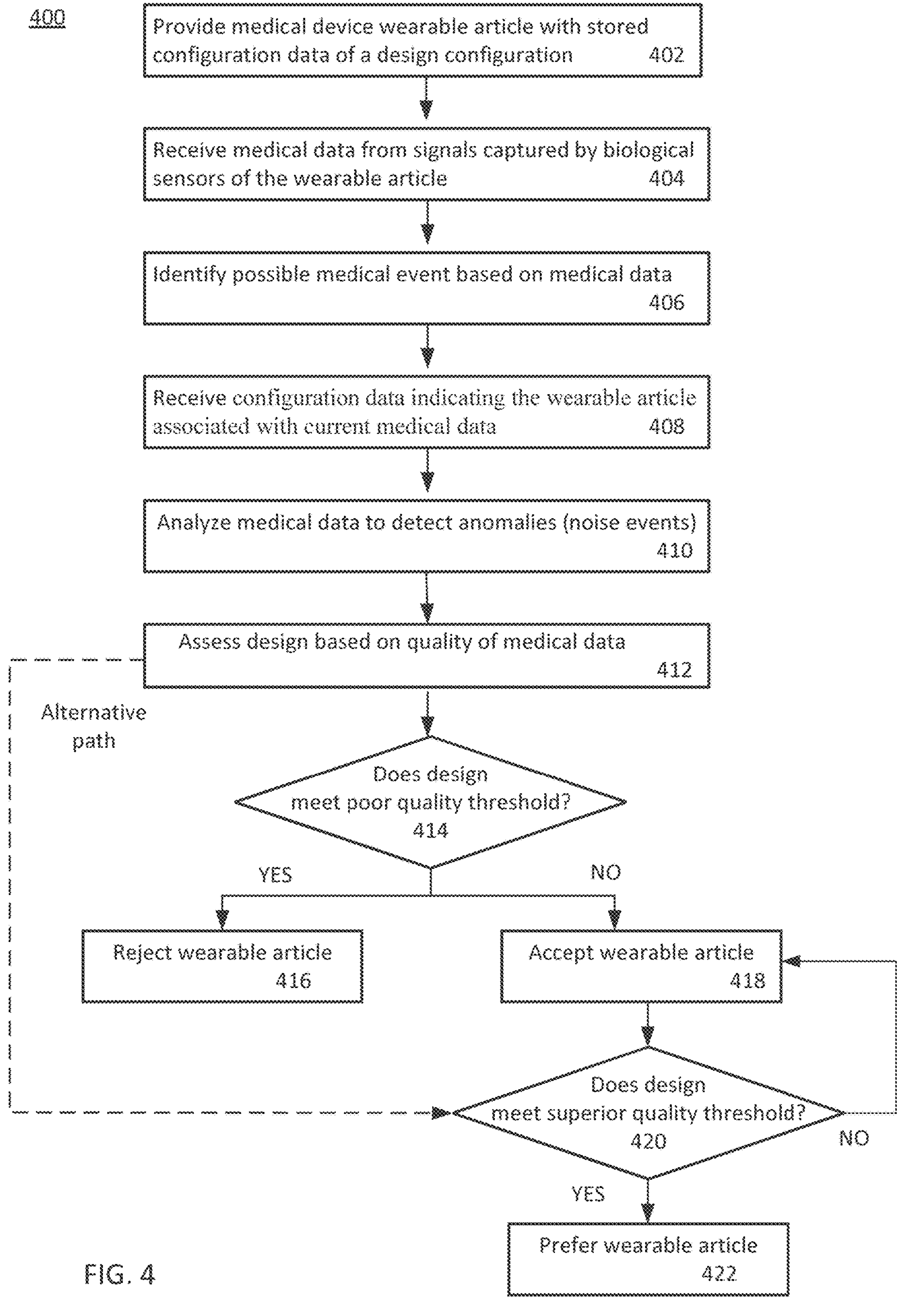
FIG. 4 is a flowchart of an example method for evaluating a design configuration of a wearable article of a medical device, in accordance with some implementations.

FIG. 4 shows a flowchart of an example medical wearable evaluation process 400 to evaluate a design configuration of a wearable article of a medical device worn by a patient.

In block 402 at least one wearable article (and often multiple wearable articles with difference design configurations) is provided to a patient as part of a medical device. The wearable article may be associated with an identifier, such as a serial number, which may be stored as configuration data in the wearable device.

The wearable article is characterized by a design configuration while worn by the patient during a use time period. The design configuration may include specified style, size, adjustment (e.g., size), and/or other functional characteristics of the wearable article. Descriptions of the design features of the design configuration may be stored as configuration data in the wearable article. The design configuration may also include types and arrangements of sensors accommodated by the wearable article, contact placements positions, and other design features that can impact function of the wearable article. Adjustments made to the initial design configuration wearable article after the initial onset of use may start a new use time period for the adjusted design configuration and stored as configuration data in the wearable article. In this manner, the configuration data may be updated with adjustment information at the onset of a new use time period.

In block 404 various biological sensors associated with the wearable article capture signals that reflect various parameters of the patient and form medical data. The medical data are transferred to be received by other electronic component(s) (e.g., a hub, main unit, personal computing device, remote computing device, etc.) of the medical device.

In block 406, the medical data are analyzed to identify possible medical events. The medical data may suggest a medical event had been experienced by the patient. Medical events identification is based on event criteria that is specific for the medical condition being monitored. Typically, medical events are considered clinically significant and require careful monitoring to determine treatment. Examples of cardiac related medical events that may be indicated by the medical data may include ventricular fibrillation (VF), supraventricular tachycardia (SVT), ventricular tachycardia (VT) and other heart related conditions. Other types of health events are possible, such as sleep apnea, hypopnea, and respiratory effort related arousal (RERA).

The evaluation system accesses the configuration data stored in the wearable article, in block 408. In some implementations, the configuration data may be included in medical event logs and reports on the patient health status. Such logs and reports may be sent on a regular basis to various evaluation system components, such as the remote computing device. In some implementations, a patient communication device (e.g., 114 in FIG. 1) may pull medical data from the medical device regularly, and often the medical data can be pulled at a high frequency like a couple of times per minute or similar high frequency extraction times.

The configuration data is interpreted to indicate that a particular wearable article and/or design configuration of a wearable article is in-use during collection of a set of medical data. For example, the time that medical data is collected, such as the time signals are capture by sensors for the medical data may be determined. In some implementations, a time stamp associated with the medical data may be used to indicate a medical data time. The medical data time may be compared to the use time period associated with the configuration data extracted from the wearable article to determine that the medical data was collected within the use time period for a particular wearable article. In this manner, it may be determined that the particular wearable article was in use at the time the medical data was collected.

In some implementations, the configuration data includes a wearable article identifier. The identified wearable article can be cross-referenced with a database of design configuration information for particular wearable articles at the onset of use of the wearable article or onset of a functional alteration of the wearable article. In still some implementations, the configuration data may include particular aspects of the design configuration, such as sensor types, arrangements, placements, etc. At times, configuration data may be updated with manual adjustments that effect function of the wearable article, such as adjusting the size/fit of the wearable article during a use time period and an indication of a new/updated use time period may be specified in the configuration data to indicate when the wearable article was adjusted. For example, a provider, caregiver, or patient may make such a size adjustment and enter the adjustment data into the memory of the wearable article as well as a time such adjustment was made.

In some implementations, the configuration data and set of medical data may be received at least substantially concurrent in time, or the configuration data may be received shortly after the time that a medical event is identified, indicating correlation of the configuration data and the medical data. For example, upon identification of a possible medical event represented in a set of medical data, the medical device may pull configuration data from the memory of the wearable article. In some implementations, an algorithm configured to identify a wearable article and/or design configuration may pair the wearable article specified in the configuration data to the specific set of medical data by inferring a lag time between retrieving the configuration data and receipt of the medical data. For example, the evaluation system may presume it takes a certain number of seconds to retrieve configuration data after medical data is received (or vice versa) by the evaluation module(s) (such as item 606 in FIG. 6 described below).

In block 410, a set of medical data that correlates with a possible medical event is analyzed for accuracy in representing the possible medical event. Anomaly events in the medical data, such as noise events, may be detected and skew the representation of the possible medical event. The extent of the anomalies in the set of medical data may also be assessed. Medical events are typically determined by medical data being consistent with identification of the medical event. However, noise events may decrease the accuracy of the medical data so that a possible medical event as indicated by the medical data may be a glitch rather than an actual medical event of the patient. For example, a heart rate reading that may be indicative of a possible cardiac medical event, such as a heart rate of 190, may not be sustained long enough to be consistent with an actual cardiac medical event that would trigger a shock treatment. The heart rate medical data may be found to include an anomaly. Some anomalies may be unrelated to design characteristics, such as a patient movement causing short bursts of a threshold heart rate and the heartrate may then quickly slow down again, as represented in the medical data.

In some cases, the medical data may be analyzed by a noise detection algorithm, such as a software program running in the main unit, personal communication device, or remote computing device. The noise detection algorithm may save noise event data, which is identified as anomalies that do not trigger treatment action. When noise events are detected, it is beneficial for the evaluation system to determine a cause of the noise. Such analysis of medical data to detect anomalies may be also be performed manually by a provider and the result transmitted to the medical device for the design evaluation.

In some implementations different types of sensors may be accommodated by various design configurations of wearable articles. The noise detection algorithm may turn on and off particular code sections depending on the type of medical data collected by the different sensors used in a design configuration of a subject wearable article. For example, a code section for medical data captured by a wearable article that includes Saturation of Peripheral Oxygen (SPO2) sensors for oxygen hemoglobin detection may be run whereas the same code section may be ignored for other medical data of another wearable article that does not include the SPO2 sensors. Such control of software run for medical data analysis from certain sensors employed by different wearable articles can avoid software errors due to the software attempting to analyze medical data from a non-used sensor.

In block 412 quality assessment is performed to determine a design configuration that contributes to, e.g., causes or otherwise impacts, the occurrences of anomalies by interfering with the capture of signals for medical data. In some implementations, the causal relationship between a design configuration and data anomalies may include comparing patterns of presently detected data anomalies with previously detected anomalies for the patient, for example, while the patient had worn the same wearable article or a different wearable article having the same design configuration or different design configuration. In some techniques to determine a causal relationship, the design configuration of the subject wearable article may be compared to noise events that have been previously correlated with other design configurations. Where previous design configurations do not result in the same or similar amount of noise, the subject design configuration may be a cause of the detected noise.

Comparisons between medical data from corresponding sensors, e.g., electrodes, between wearable articles may take into consideration the impact of different design features of the captured data. In some implementations, various wearable articles may be a same style that is differently sized. The medical data may be analyzed by performing normalization techniques, such as z-score normalization, linear normalization, etc., to adjust for different contact positions of corresponding electrodes of the wearable articles due to the different sizes of the wearable articles. Similarly, design configurations may include different types of wearable articles. In such instances, medical data may be analyzed by performing normalization techniques, such as z-score normalization, linear normalization, etc., to adjust for different contact positions of the corresponding electrodes of the wearable articles due to the different types of the wearable articles.

In some implementations, an evaluation artificial intelligence (AI) model may be employed to predict whether a design configuration contributes to data anomalies, and/or an extent of such contribution. The evaluation AI model is trained with training data sets that may include past configuration data and anomaly event data, e.g., noise data, of the subject patient and/or other patients having similar characteristics as the subject patient, such as similar build, medical condition, lifestyles, etc. The current data anomalies and design configuration data may be input to the AI model and output may be received as a prediction of whether the subject design configuration may contribute in the future to poor quality medical data (meets a poor quality threshold) and/or confirmation that the design configuration has contributed to detected anomaly events, e.g., noise, by the quality threshold amount. In some implementations, the evaluation AI model may also/or predict an extent that a design configuration has or will contribute to poor quality medical data.

The AI model can further determine which design feature or combinations of design features of a plurality of design features embodied in the design configuration contributed to the poor quality (meeting of the poor quality threshold). Design features may include wearable article sizes, styles, types, sensor arrangement, sensor types, other features built into the wearable article that affect function, and combinations thereof. The AI model may be trained with training data sets of previously used combinations of design features to analyze patterns and predict which of the design features are more incline to result in a particular quality of medical data. Other methods that use or do not use AI models, for isolating design features that contribute to poor or superior quality medical data may be employed such as comparing specific design features that result in various qualities of medical data.

Determining which design features or combinations of the design features contribute to a particular result may assist in designing better performing wearable articles, or otherwise choosing a better wearable article for a patient to wear. A determined preferred combination of design features may pick design features from various design configurations of wearable articles to create a new design configuration for future manufacture of wearable articles or adjustments to be made to current wearable articles.

In decision block 414, a determination is made as to whether the design configuration contributes to poor quality medical data to a predefined threshold level (extent) for a patient. For example, it may be determined whether a design configuration contributes to anomalies in the medical data, such as noise events, by a poor quality threshold amount. If the design configuration does not meet (including fall below) the poor quality threshold, e.g., the design configuration, the wearable article having the design configuration may be accepted in block 418.

In some implementations, it may be tolerable that the design configuration contributes to poor medical data to an acceptable amount (within an acceptable threshold amount). For example, a design configuration may not be rejected where a sufficiently accurate detection of a medical event may still be made despite some interference from the design configuration of the wearable article.

In some implementations, the process may proceed to decision block 420 to determine if the design configuration is optimal as meeting (including exceeding) a superior quality threshold amount. For example, if the medical data is found to have few or no anomalies and accurately reflect the patient's parameters to a superior threshold amount, the design configuration and wearable article associated with the medical data may be determined to be optimal and preferred for the patient in block 422. In some implementations, a notification of the preferred wearable article may be provided to the patient, provider, care taker or other interested party. Notification may optionally suggest continued use of the preferred wearable article and/or trigger providing of additional wearable articles of the optimal design configuration to the patient.

A certain amount of noise associated with a design configuration may be deemed acceptable and not result in rejection of the wearable article. Above such a noise amount, the wearable article may be rejected. If the poor quality threshold is met by the design configuration, the wearable article associated with the design configuration is rejected in block 416. In the case of rejection of the wearable article, a notification of rejection of a wearable article may be provided to the patient, provider, caretaker or other interested party. Such notification may advise an adjustment to be made to the wearable article to improve the design configuration. Notification may optionally suggest discontinued use of the rejected wearable article and/or to swap the wearable article with another wearable article having a different design configuration. In some cases, rejection of a wearable article, may trigger a new wearable article having an acceptable design configuration to be delivered to the patient.

In some implementations, certain aspects of a design configuration may be identified as having contributed to poor performance, acceptable performance, and/or superior performance of a wearable article. For example, analysis of the medical data quality may be compared with previously achieved medical data quality for the patient in specific design aspects such as sensor types, sensor arrangement, wearable article size, etc.

In some implementations, an alternative path (denoted in FIG. 4 by dotted line) may be taken from block 412, where the process skips blocks 414, 416, and 418 and does not include a determination of the design configuration contributing to poor quality data. Instead the process proceeds to make a determination of superior quality of the medical data due to a design configuration as in blocks 420 and 422.

Some or all of the evaluation process 400, or any other processes described herein, or variations and/or combinations of those processes, may be performed under the control of one or more computer systems configured with executable instructions and/or other data, and may be implemented as executable instructions executing collectively on one or more processors. For example, the evaluation process 400 may be adapted to include steps for treating a patient, such as a defibrillator shock based on the determined episodes.

Figure 5:
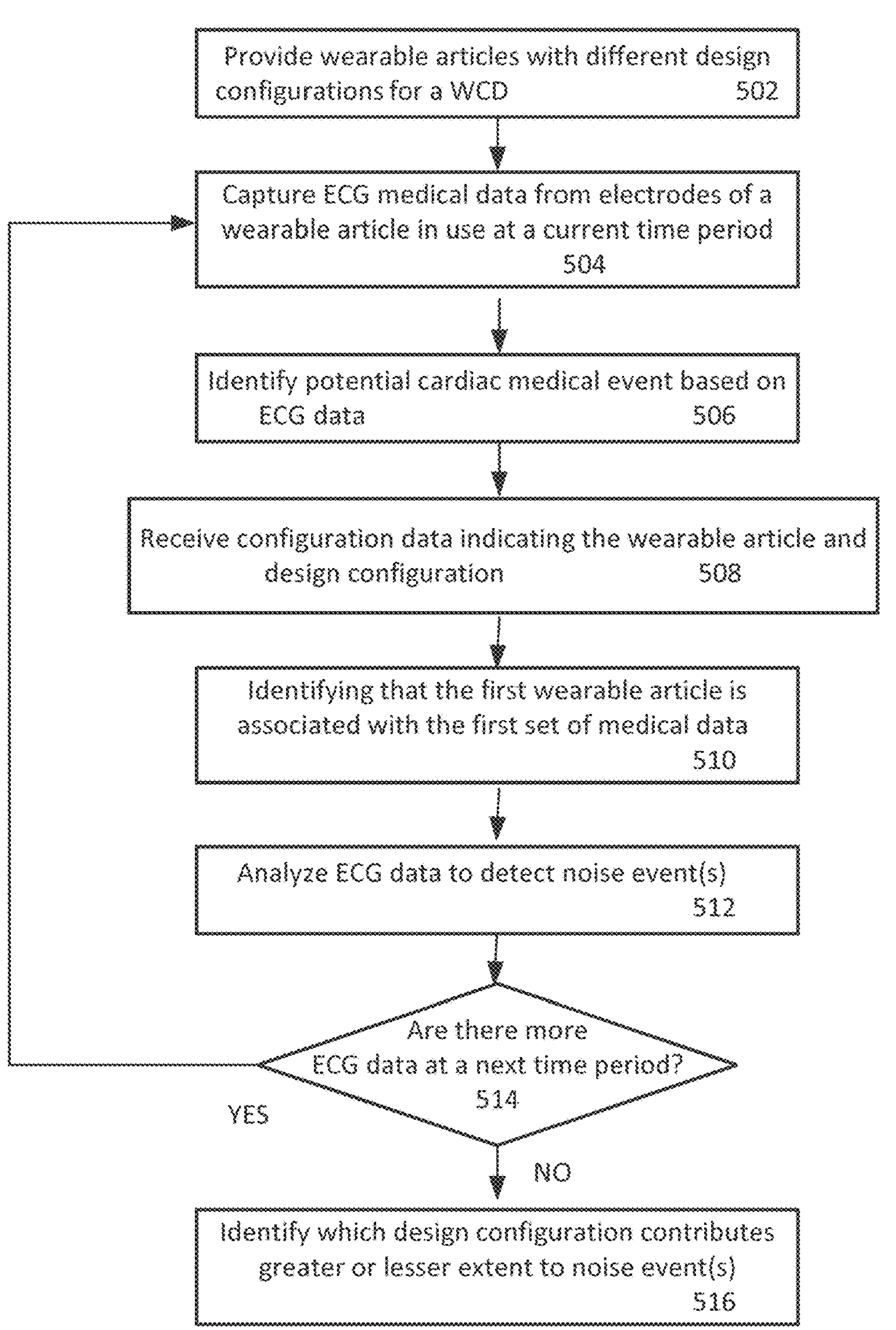
FIG. 5 is a flowchart of an example method for comparing design configurations of wearable articles in wearable cardioverter defibrillator (WCD) devices, in accordance with some implementations.

FIG. 5 shows a flowchart of an example method for comparing design configurations of wearable articles used in wearable cardioverter defibrillator (WCD) devices. In block 502 multiple wearable articles are provided to a patient with individual design configurations. At least two of the wearable articles have different design configurations, which are described in stored configuration data. At least some of the configuration data, such as identifiers of the wearable articles are stored locally in a memory device of the wearable article. In some implementations, a locally stored wearable article identifier may be retrieved and cross referenced with design configuration details in configuration data corresponding to the identifier and stored external to the wearable article, such as in a database stored in an electronic module (e.g., 120 in FIG. 1), main unit (e.g., 112 in FIG. 1), and/or remote computing device (e.g., 130 in FIG. 1) of the evaluation system. In some implementations, locally stored configuration data (in a memory of the wearable article) may include current design configuration details for the wearable article, which may include time period of use and updated configuration data such as size adjustments made to the wearable article.

In block 504, ECG medical data signals are captured from electrodes of a wearable article that is in use, being worn by the patient during a current time period. Sets of the ECG medical data are analyzed in block 506 to spot a potential cardiac medical event that may be currently experienced by the patient.

In block 508, configuration data is received from the wearable article storage. The configuration data indicates the design configuration and/or which of the wearable articles assigned to the patient is associated with current ECG data. For example, the configuration data may include a wearable article identifier such as a serial number of the wearable article, which may be cross-referenced to a corresponding design configuration of the wearable article. In some implementations, the design configuration may be included in the configuration data to characterize the design of the wearable article.

In block 510, the retrieved configuration data, at least one of the wearable articles and/or design configurations of the wearable article(s) are identified as being associated with the first set of medical data captured during the use time period that the wearable article was worn and used to capture medical data by the patient.

In block 512, ECG data are further analyzed to determine quality of the medical data, such as detecting any noise event(s) in the medical data. In some implementations, a provider may review the medical data or an algorithm of the system may perform the determination of noise events. A degree or level of noise events may be found, such as a percentage of the medical data that is considered noise.

In decision block 514, it is determined whether there are more ECG medical data at a next time period. Often, the patient wears a wearable article for a use time period. The patient then swaps wearable articles to use a next wearable article during a next time period.

In block 516, a determination is made as to an extent that each design configuration contributes to a quality of the sets of medical data collected in block 504. The amount of noise data present in the medical data is determined. In some implementations, a first design configuration may be found to meet a poor quality threshold by contributing to medical data anomalies by a certain amount. As a result, the first design configuration may be rejected. A second design configuration may not meet the poor quality threshold and may be accepted.

In some implementations, characteristics of a design configuration may be specified and the system may identify which aspects of the design configuration of wearable articles contribute to superior medical data (e.g., acceptable medical data), poor medical data (e.g., rejectable medical data). For example, the system may compare design configurations of various wearable articles used by a patient and determine that the design configurations that include an aspect of specific type of sensor, specific sensor arrangement, etc. results in high level of noise events, the system may determine that such aspect is not optimal. Often, an ill-fitting wearable article can result in high noise events. The system may transmit a notification of the results of the evaluation, such as identifying a design configuration (e.g., all aspects of a design or certain aspects of a design configuration) and/or wearable article having the design configuration).

The evaluation system identifies design configurations as accepted, rejected, and/or preferred based on the determination step in block 516. The system may determine that a particular design configuration of a wearable article contributes to anomalies in the medical data to a greater or lesser extent than a different design configuration of another wearable article. In this manner, a preference may be identified for one wearable article having a design configuration over another wearable article with a different design configuration. In some implementations, the extent of the contribution to anomaly events may need to meet a threshold comparative amount in order to identify a preference of one over another.

While the implementations of FIG. 5 is directed to monitoring devices for cardiac monitoring and capturing ECG data, other implementations include medical devices having one or more implanted sensors for which ECG and/or other physiological waveform data is collected and can be displayed. In view of the present disclosure, the above-described implementations of medical data can be adapted for waveforms other than ECG. For example, such data can include but are not limited to: electroencephalogram (EEG), capnography, electrodermal activity (EDA), transthoracic impedance (TTI), photoplethysmography, SpO2, heart-sound/phonocardiogram, electromyography (EMG), etc.

The evaluation processes represented in FIGS. 4 and 5 are often implemented by various components of the medical device (for example, 104 in FIG. 1). Certain steps can also be offloaded by the wearable medical device to various computing devices, such as an application running on a dedicated server, e.g., remote computing device, and/or an application hosted in the cloud. In implementations, the device or devices implementing the medical wearable evaluation process can be stand-alone or a combination of mobile processing and cloud processing. According to this description, the medical device performs steps to collect medical data (e.g., ECG data) and wearable article configuration data for analysis and evaluation of performance contribution of the design configurations associated with each wearable article.

Figure 6:
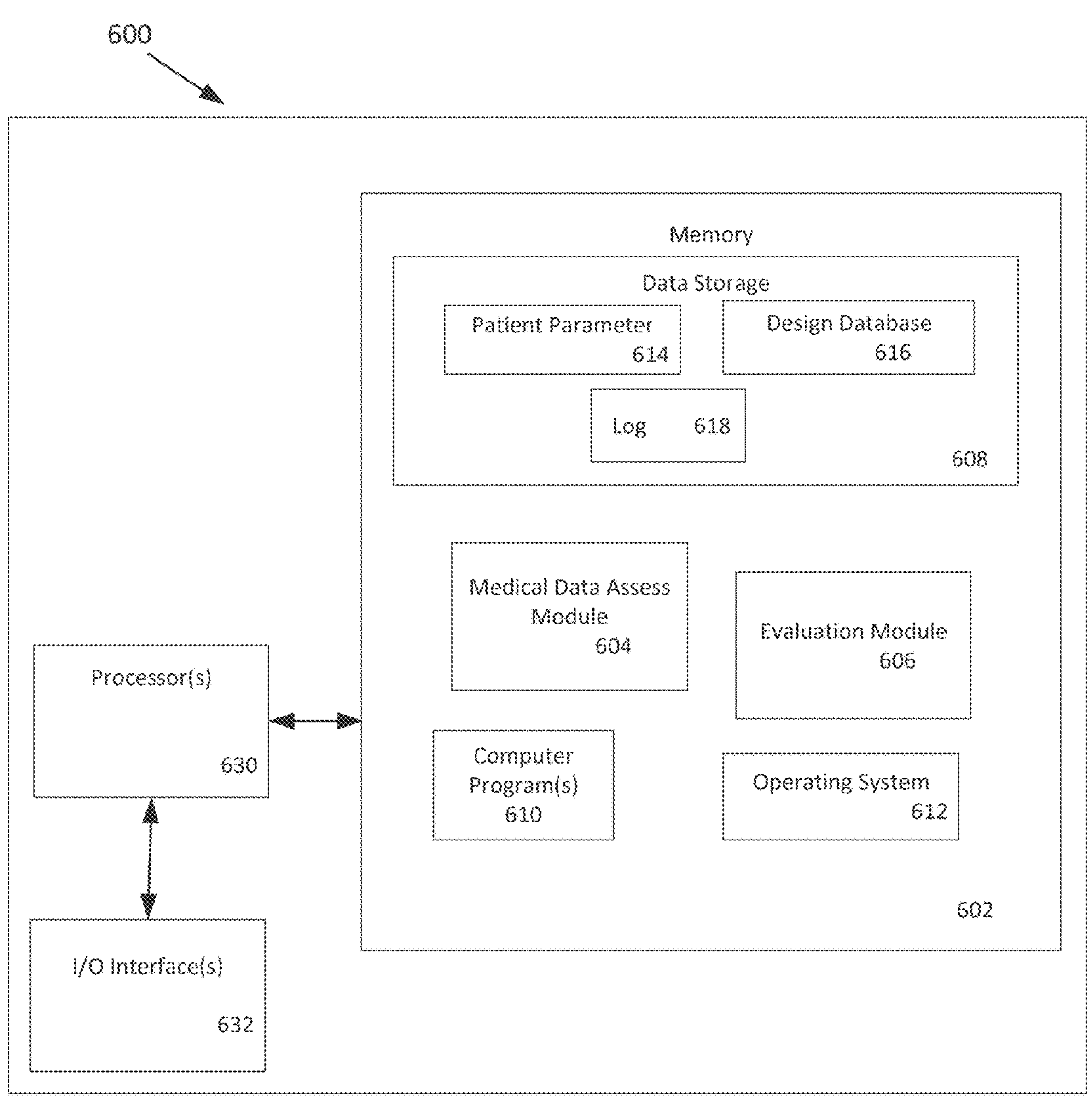
FIG. 6 is a block diagram illustrating an example computing device upon which at least some of the medical wearable evaluation processes may be implemented, in accordance with some implementations.

FIG. 6 shows example medical device component(s), which may implement at least some of the medical wearable evaluation processes described herein. In some implementations, computer device 600 may represent electronic module 120 and/or main unit 112 of FIG. 1. The computer device 600 may include memory 602, processor 630, and I/O interface 632. The various elements of the computing device 600 are shown in FIG. 6 as discrete/separate elements for purposes of illustration and explanation. According to some implementations, it is possible to combine some of these elements into a single element or device. Additional components may also be included in the computing device 600. Components shown for computing device 600 may also be split between multiple computing devices, such as electronic module 120, main unit 112, remote computing device 130, and other electronic components. According to some implementations, it is possible to combine some of these elements into a single element or device, while in other implementations of the evaluation system, these elements may be distributed across a network such as in a cloud computing network. For example, functions of the evaluation system may be performed by one or more remote computing device in a distributed network to provide information to medical device as a service.

The memory 602 of the computing device 600 is for storing information within the computing device 600. Memory 602 may be a random access memory (RAM) or other dynamic storage device, coupled to a bus for storing information and instructions to be executed by the processor 630. The memory 602 may also be used for storing temporary variables or other intermediate information during execution of instructions to be executed by the processor 630. Such instructions, when stored in non-transitory storage media accessible to the processor 630, render the client computer system 600 into a special-purpose machine that is customized to perform the operations specified in the instructions.

The memory 602 may be any suitable data storage, memory and/or non-transitory computer-readable storage media, including electronic storage devices such as random-access memory (RAM), read-only memory (ROM), magnetic storage device (hard disk drive or the like), flash, optical storage device (CD, DVD or the like), magnetic or optical disk, or other tangible media suitable for storing instructions (e.g., program or software instructions) for execution by the processor 630. For example, a tangible medium such as a hardware storage device can be used to store the control logic, which can include executable instructions. The instructions can also be contained in, and provided as, an electronic signal, for example in the form of software as a service (SaaS) delivered from a server (e.g., a distributed system and/or a cloud computing system).

Data storage 608 may store various data including a database having design feature data 616 for configuration data of wearable articles, patient parameter 614, various logs 618 may be stored such as a log of use times for wearable article, and other data. In some implementations, any of the various data may be stored on an external storage rather than in data store 608, such as the remote computing device or other external resource.

At least a portion of the information may also be stored on a disk drive or other computer readable storage device (not shown) within the computing device 600. Such storage device include a floppy disk device, a hard disk device, an optical disk device, or a tape device, digital cards, a flash memory or other similar solid state memory device, or an array of devices.

Various modules such as medical data evaluation module 604, and/or design evaluation module 606, and/or other computer programs 610, also referred to as programs, software, software applications or code, are stored within memory 602 and contain instructions that, when executed, perform one or more methods, such as those described herein. The computer program 610, medical data evaluation module 604, and/or design evaluation module 606 may be tangibly embodied in an information carrier such as computer or machine readable medium, for example, the memory 602, storage device or memory on processor 630. A machine readable medium is any computer program product, apparatus or device used to provide machine instructions or data to a programmable processor.

Medical data evaluation module 604 is configured to perform analysis on the medical data to determine whether the medical data represents true medical events of the patient or anomalies such as noise events, for example steps 406 and 410 of FIG. 4 and/or steps 506 and 512 of FIG. 5. Where anomalies, e.g., noise events, are detected, the medical data evaluation module 604 may be further configured to assess the nature of the anomalies, such as determine an extent of noise events (e.g., percentage of a set or sets of medical data that includes such noise events or number of noise events over a period of time), timing of such noise events, level or degree of noise events, significance of the anomalies on correctly or incorrectly detecting medical events, etc. The resulting assessment of the quality of the medical data may be provided to design evaluation module 606 to evaluate design configurations.

Design evaluation module 606 performs evaluation of the design configurations based on the medical data and configuration data, such as steps 412 and/or 414 in FIG. 4 and step 516 in FIG. 5, for example, by correlating anomalies detected by the medical data assessment results with an in-use wearable article responsible for capturing the subject medical data having the anomalies. In some implementations, the design evaluation module 606 may correlate high quality medical data, e.g., free from anomalies or significant anomalies, with an in-use wearable article responsible for capturing the high quality medical data.

Implementations that employ AI model(s) may include such AI model to facilitate evaluation of the wearable article(s). For example, an evaluation AI model may predict an extent that a wearable design contributes to anomalies in a set or sets of medical data. Other AI models may be employed to facilitate various steps of the evaluation process.

One or more train and/or retrain module(s) may be further provided to input training or retraining datasets to one or more of the AI models and conduct training or retraining the AI models. However, in some implementations, training and/or retraining or an AI model may be performed by a separate computing system. In these implementations, a fully trained or retrained AI model may be provided by the separate computing system to computing device 600 for storage and use.

Any suitable programming languages and programming techniques may be used to implement the routines of particular implementations. Different programming techniques may be employed such as procedural or object-oriented. The routines may execute on a single processing device or multiple processors. Although the steps, operations, or computations may be presented in a specific order, the order may be changed in different particular implementations. In some particular implementations, multiple steps shown as sequential in this specification may be performed at the same time. A number of implementations have been described. Features described with conditional language may describe implementations that are optional. The functional blocks, methods, devices, and systems described in the present disclosure may be integrated or divided into different combinations of systems, devices, and functional blocks as would be known to those skilled in the art.

The computing device 600 may implement the techniques described herein using customized hard-wired logic, one or more ASICs or FPGAs, firmware and/or program logic which in combination with the computer system causes or programs the computing device 600 to be a special-purpose machine. According to one implementation, the techniques herein are performed by the computing device 600 in response to the processor 630 executing one or more sequences of one or more instructions contained in the memory 602. Such instructions may be read into the memory 602 from another storage medium. Execution of the sequences of instructions contained in the memory 602 causes the processor 630 to perform the process steps described herein.

In alternative implementations, one or more methods can be implemented in hardware (logic gates, etc.), or in a combination of hardware and software. Example hardware can be programmable processors (e.g. Field-Programmable Gate Array (FPGA), Complex Programmable Logic Device), general purpose processors, graphics processing units (GPUs), Application Specific Integrated Circuits (ASICs), and the like. One or more methods can be performed as part of or component of an application running on the system, or as an application or software running in conjunction with other applications and operating system 612. Any operating system 612, e.g., mobile operating system, that is supports the evaluation processes described herein performed by the computing device 600 may be employed.

The term "storage media" as used herein refers to any non-transitory media that store data and/or instructions that cause a machine to operate in a specific fashion. Such storage media may include non-volatile media and/or volatile media. Non-volatile media includes, for example, optical or magnetic disks. Volatile media includes dynamic memory, such as the memory 602. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, an EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire, and fiber optics, including the wires that include the bus. Transmission media can also take the form of acoustic or light waves, such as those generated during radio-wave and infra-red data communications.

Various forms of media may be involved in carrying one or more sequences of one or more instructions to the processor 630 for execution. For example, the instructions may initially be carried on a magnetic disk or solid state drive of a remote computer. The remote computer can load the instructions into its dynamic memory and send the instructions over a network connection. A modem or network interface local to the computing device 600 can receive the data. The bus carries the data to the memory 602, from which the processor 630 retrieves and executes the instructions. The instructions received by the memory 602 may optionally be stored on a storage device either before or after execution by the processor 630.

The processor 630 may process instruction for execution within the computing device 600 including instructions stored in memory 602 or on the data store 608. The processor 630 may coordinate computing device components, e.g. applications, wireless or wired communication through interfaces, etc. In some implementations, multiple processors and buses may be used.

The processor 630 may be implemented as a chipset of chips that include separate and multiple analog digital processors. The processor may also be implemented using various architectures. For example, the processor 630 may be a CISC (Complex Instruction Set Computer) processor, RISC (Reduced Instruction Set Computer) processor or MISC (Minimal Instruction Set Computer) processor, mobile device processors, etc.

The "processor" as used herein, includes any suitable hardware and/or software system, mechanism or component that processes data, signals or other information. A processor may include a system with a general-purpose central processing unit, multiple processing units, dedicated circuitry for achieving functionality, or other systems. Processing need not be limited to a geographic location, or have temporal limitations. For example, a processor may perform its functions in "real-time," "offline," in a "batch mode," etc. Portions of processing may be performed at different times and at different locations, by different (or the same) processing systems.

The Input/Output (I/O) interface 632 can interface to other input and output devices. In some implementations, the I/O interface 632 can connect to interface devices such as input devices (keyboard, pointing device, touchscreen, microphone, camera, scanner, sensors, etc.) and/or output devices (display devices, speaker devices, printers, motors, etc.). Some implementations can provide a microphone for capturing sound (e.g., as a part of captured images, voice commands, etc.), audio speaker devices for outputting sound, or other input and output devices.

The devices and/or systems described in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described above. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations that may be provided within at least one non-transitory, tangible, computer readable medium for execution by the one or more processors. Flowcharts as in FIGS. 4 and 5 are used to describe both programs and also methods. So, while flowcharts described methods in terms of blocks, they also concurrently describe programs.

Other implementations include combinations and sub-combinations of features described or shown in the drawings herein, including for example, implementations that are equivalent to: providing or applying a feature in a different order than in a described implementation, extracting an individual feature from one and inserting such feature into another implementations; removing one or more features from an implementation; or both removing one or more features from an implementation and adding one or more features extracted from one or more other implementations, while providing the advantages of the features incorporated in such combinations and sub-combinations. As used in this paragraph, feature or features can refer to the structures and/or functions of an apparatus, article of manufacture or system, and/or the steps, acts, or modalities of a method.

What is claimed is:

1. A method for optimizing performance of a cardioverter defibrillator system to treat a cardiac condition of a patient, the method comprising:

providing the cardioverter defibrillator system including a first wearable article having a first design configuration with first cardiac treatment components and a second wearable article having a second design configuration different from the first design configuration with second cardiac treatment components;

receiving a first set of electrocardiogram (ECG) data having first data anomalies from first signals captured by first electrodes of the first wearable article being worn by the patient during a first use time period;

determining from first configuration data received from the first wearable article while in use that the first wearable article is associated with the first set of ECG data;

determining that the first design configuration contributes to the first data anomalies by a first extent;

receiving a second set of ECG data having second data anomalies from second signals captured by second electrodes of the second wearable article being worn by the patient during a second use time period;

determining from second configuration data received from the second wearable article while in use that the second wearable article is associated with the second set of ECG data;

determining that the second design configuration contributes to the second data anomalies by a second extent;

determining an acceptable wearable article by:

determining which of the first extent and second extent is greater;

accepting the first wearable article when the second extent is determined to be greater than the first extent accepting the second wearable article when the first extent is determined to be greater than the second extent; and administering the cardiovascular treatment by the cardiac treatment components of the accepted first wearable article in response to the first set of ECG data indicating a treatable medical event, or the accepted second wearable article in response to the second set of ECG data indicating a treatable medical event.

2. The method of claim 1, wherein the first configuration data includes an indication of the first use time period and the second configuration data includes an indication of the second use time period, and wherein the first configuration data and second configuration data are further selected from a group of: at least one wearable article identifier, at least one design feature, and combinations thereof.

3. The method of claim 2, wherein the first configuration data and/or second configuration data include the at least one design feature selected from the group of: a wearable size, a wearable size adjustment, a wearable style, a biological sensor arrangement, biological sensor contact placement, biological sensor type, and combinations thereof.

4. The method of claim 1, wherein the first design configuration and the second design configuration include different respective sizes of a same style of wearable article, and wherein determining the acceptable wearable article includes normalizing the first set of ECG data and the second set of ECG data to adjust for different contact positions of the first electrodes and the second electrodes due to the different respective sizes and/or different respective types.

5. The method of claim 1, wherein the second wearable article is accepted, and the method further comprises transmitting a notification to enable the patient to use the second wearable article having the second design configuration.

6. The method of claim 1, further comprising:

determining from the configuration data that while the first wearable article is in use, an adjustment is intentionally made to a design feature of the design configuration of the first wearable article;

responsive to detecting the adjustment, restarting the first use time period, wherein the first set of ECG data includes updated ECG data for the restarted first use time period and the configuration data includes an indication of the adjustment and time of the adjustment;

determining that the adjustment contributes to the first data anomalies to a third extent; and in response to determining the third extent, providing instruction to change or maintain the adjustment.

7. A cardioverter defibrillator system to treat a cardiac condition of a patient, the system comprising:

at least two wearable articles including a first wearable article having a first design configuration with first cardiac treatment components and accommodating first biological sensors, and a second wearable article having a second design configuration with second cardiac treatment components and accommodating second biological sensors;

at least one computing device comprising:

an interface for receiving medical data and configuration data; and one or more processors and logic encoded in one or more non-transitory media for execution by the one or more processors and when executed operable to perform steps comprising:

receiving a first set of the medical data having first data anomalies from signals captured by first biological sensors of the first wearable article being worn by the patient during a first use time period;

determining from first configuration data received from the first wearable article while in use that the first wearable article is associated with the first set of medical data;

determining that the first design configuration contributes to the first data anomalies by a first extent;

receiving a second set of the medical data having second data anomalies from signals captured by second biological sensors of the second wearable article being worn by the patient during a second use time period;

determining from second configuration data received from the second wearable article while in use that the second wearable article is associated with the second set of medical data;

determining that the second design configuration contributes to the second data anomalies by a second extent;

determining an acceptable wearable article by:

determining which of the first extent and second extent is greater;

accepting the first wearable article when the second extent is determined to be greater than the first extent accepting the second wearable article when the first extent is determined to be greater than the second extent wherein the cardiovascular treatment is administered by the cardiac treatment components of: the accepted first wearable article in response to the first set of medical data indicating a treatable medical event, or the accepted second wearable article in response the second set of medical data indicating a treatable medical event.

8. The system of claim 7, wherein the first wearable article includes a first memory device to store the first configuration data, and the second wearable article includes a second memory device to store the second configuration data.

9. The system of claim 8, wherein the first configuration data includes an indication of the first use time period and the second configuration data includes an indication of the second use time period, and wherein the first configuration data and the second configuration data are further selected from a group of: at least one wearable article identifier, at least one design feature, and combinations thereof.

10. The system of claim 9, wherein the first configuration data and the second configuration data include the at least one design feature selected from the group of: a wearable article manufacturer, a wearable size, a wearable size adjustment, a wearable style, a biological sensor arrangement, biological sensor contact placement, a biological sensor type, and combinations thereof.

11. The system of claim 7, wherein the first design configuration and the second design configuration include different respective sizes of a same style of wearable article, and wherein the steps that the logic is operable to perform further include normalizing the first set of medical data and the second set of medical data to adjust for different contact positions of the first biological sensors and second biological sensors due to the different respective sizes and/or different respective styles.

12. The system of claim 7, wherein a different type of sensor of the first biological sensors captures a first medical data type included in the first set of medical data, and wherein the second set of medical data captured by the second biological sensors excludes the first medical data type, and wherein an algorithm used for the analyzing of the second set of medical data ignores calculations for the different type of sensor of the first biological sensors.

13. The system of claim 7, wherein the interface is configured to a transmit a notification that the first design configuration or the second design configuration is preferred in response to determining the acceptable wearable article.

14. A method for optimizing performance of a medical treatment system to treat a medical condition of a patient, the method comprising:

providing the medical treatment system including a wearable article having a first design configuration with medical treatment components;

receiving a set of medical data from biological sensors of the wearable article being worn by the patient during a use time period;

receiving from the wearable article, configuration data indicating the wearable article is associated with the set of medical data;

determining an acceptable wearable article by:

determining that the first design configuration meets a poor quality threshold by contributing to data anomalies or the first design configuration meets a superior quality threshold;

accepting an alternate wearable article having alternate medical treatment components with a different design configuration and rejecting the first design configuration, when the first design configuration is determined to meet the poor quality threshold; and accepting the first design configuration when the first design configuration is determined to meet the superior quality threshold; and administering the medical treatment by the corresponding medical treatment components of the accepted wearable article in response to medical data from the accepted wearable article indicating a treatable medical event.

15. The method of claim 14, wherein the configuration data includes an indication of the use time period that matches with a time of capture of the set of medical data, and wherein the configuration data is further selected from a group of: at least one wearable article identifier, at least one design feature, and combinations thereof.

16. The method of claim 14, where the design configuration is determined to meet the poor quality threshold and in response, the method further comprises transmitting a notification to enable the patient to use the alternate wearable article having the different design configuration.

17. The method of claim 14, where the first design configuration is determined to meet the superior quality threshold and in response, the method further comprises transmitting a notification to enable the patient to use an additional wearable article having a same design configuration.

18. The method of claim 14, further comprising determining one or more design features of a plurality of design features of the design configuration that contribute to meeting of the poor quality threshold by the first design configuration.

19. The method of claim 14, further comprising:

determining from the configuration data that while the first wearable article is in use, an adjustment is intentionally made to a design feature of the design configuration of the first wearable article;

responsive to detecting the adjustment, restarting the use time period, wherein the medical data includes updated medical data for the restarted use time period and the configuration data includes an indication of the adjustment and time of the adjustment; and determining that the adjustment contributes to the data anomalies to meet the poor quality threshold and provide instruction to change the adjustment.

* * * * *